United States Patent
Chandler

(10) Patent No.: US 10,760,853 B1
(45) Date of Patent: Sep. 1, 2020

(54) AUTOMATED THERMAL EXCHANGE SYSTEM FOR AUTOCLAVE STERILIZER

(71) Applicant: Crosstex International, Inc., Hauppauge, NY (US)

(72) Inventor: James W. Chandler, Ashland, OH (US)

(73) Assignee: Crosstex International, Inc., Hauppauge, NY (US)

( * ) Notice: Subject to any disclaimer, the term of this patent is extended or adjusted under 35 U.S.C. 154(b) by 498 days.

(21) Appl. No.: 15/191,695

(22) Filed: Jun. 24, 2016

Related U.S. Application Data

(63) Continuation-in-part of application No. 13/774,841, filed on Feb. 22, 2013, now abandoned.

(60) Provisional application No. 62/256,917, filed on Nov. 18, 2015, provisional application No. 61/611,086, filed on Mar. 15, 2012.

(51) Int. Cl.
| | |
|---|---|
| *F28D 1/02* | (2006.01) |
| *F28D 1/047* | (2006.01) |
| *F28F 27/02* | (2006.01) |
| *F16K 31/00* | (2006.01) |
| *F16K 37/00* | (2006.01) |
| *F16K 1/12* | (2006.01) |
| *F28B 1/02* | (2006.01) |
| *A61L 2/20* | (2006.01) |

(52) U.S. Cl.
CPC .............. *F28D 1/0206* (2013.01); *A61L 2/20* (2013.01); *F16K 1/12* (2013.01); *F16K 31/002* (2013.01); *F16K 37/0058* (2013.01); *F28B 1/02* (2013.01); *F28D 1/0472* (2013.01); *F28F 27/02* (2013.01); *F28F 2230/00* (2013.01); *F28F 2275/20* (2013.01)

(58) Field of Classification Search
CPC ........ F28D 1/0206; F28D 1/0472; A61L 2/20; F28B 1/02; F16K 37/0058; F16K 31/002; F16K 1/12; F28F 27/02; F28F 2275/20; F28F 2230/00
See application file for complete search history.

(56) References Cited

U.S. PATENT DOCUMENTS

| | | | | |
|---|---|---|---|---|
| 3,065,509 A | * | 11/1962 | Vischer, Jr. ............... | A61L 2/07 422/295 |
| 3,347,619 A | * | 10/1967 | Vischer ..................... | A61L 2/07 251/282 |
| 3,366,442 A | * | 1/1968 | Neiss ........................ | A23L 3/10 165/104.31 |
| 3,681,008 A | * | 8/1972 | Black ........................ | A61L 2/07 220/240 |
| 3,717,434 A | * | 2/1973 | Black ........................ | A61L 2/07 422/112 |

(Continued)

*Primary Examiner* — Ljiljana V. Ciric

(57) ABSTRACT

A system for condensing steam from an autoclave sterilizer includes a cooling tank and a condensing coil extending into the cooling tank. Cooling water from a source of water flows into the tank to cool the condensing coil when the temperature of the coolant in the cooling tank exceeds a predetermined value. A waste water drain is in fluid communication with the cooling tank. An air gap is located between the tank and the source of cooling water. The air gap includes an opening to atmospheric air and is configured to avoid back flow from a waste water drain toward the water source. A check valve may be used with or in lieu of an air gap to prevent back flow toward the water source.

28 Claims, 25 Drawing Sheets

(56) References Cited

U.S. PATENT DOCUMENTS

| | | | | |
|---|---|---|---|---|
| 3,826,612 | A * | 7/1974 | Black | A61L 2/07 422/112 |
| 3,884,636 | A * | 5/1975 | Knoblauch | A61L 2/07 422/111 |
| 5,637,280 | A * | 6/1997 | Nevell | A61L 2/04 219/430 |
| 5,681,459 | A * | 10/1997 | Bowman | B01D 61/08 137/216 |
| 5,840,248 | A * | 11/1998 | Ongaro | A61L 2/07 422/26 |
| 5,993,754 | A * | 11/1999 | Lemmen | A61L 2/26 422/293 |
| 7,476,369 | B2 * | 1/2009 | Yin | A61L 2/07 392/399 |
| 7,641,852 | B1 * | 1/2010 | McPhail | A61L 2/07 422/26 |
| 8,168,132 | B2 * | 5/2012 | Zwingenberger | A61L 2/26 422/26 |
| 2005/0045228 | A1 * | 3/2005 | Labrador | E03B 1/02 137/357 |
| 2009/0101490 | A1 * | 4/2009 | Thiers | B01D 1/305 202/166 |
| 2010/0160709 | A1 * | 6/2010 | Grierson | B01J 3/02 588/312 |
| 2010/0322830 | A1 * | 12/2010 | Moon | F28B 1/02 422/307 |
| 2012/0282153 | A1 * | 11/2012 | Cheong | F22B 1/282 422/292 |
| 2015/0021007 | A1 * | 1/2015 | Snaith | F28B 9/08 165/302 |

\* cited by examiner

AUTOMATED THERMAL EXCHANGE SYSTEM FOR AUTOCLAVE STERILIZER

CROSS-REFERENCE TO RELATED APPLICATIONS

This application claims benefit pursuant to 35 U.S.C. § 119(e) of Provisional Application 62/256,917 filed Nov. 18, 2015.

This application is a continuation-in-part of U.S. patent application Ser. No. 13/774,841 filed Feb. 22, 2013, which claims benefit under 35 U.S.C. § 119(e) of Provisional Application No. 61/611,086 filed Mar. 15, 2012. The disclosures of each of these prior applications are incorporated herein by reference in their entirety.

TECHNICAL FIELD

Exemplary embodiments relate to systems and methods for reducing the temperature of hot effluents from devices such as autoclave sterilizers for medical and dental instruments, and for delivery of such effluents to a drain or other condensate receiver while also avoiding cross connections of a source of coolant such as drinkable water, to waste drain connections.

BACKGROUND

Steam sterilizers (also called autoclaves) are used in the medical, dental, veterinarian, spa, ear-piercing and tattoo industries to sterilize the medical or dental instruments used for the patients or clients in such activities in order to prevent transfer or growth of disease organisms.

Systems for condensing the steam after it is used to sterilize such instruments may benefit from improvements.

SUMMARY

The following is a brief summary of subject matter that is described in greater detail herein. This summary is not intended to be limiting as to the scope of the claims.

A system for condensing hot water and steam from an autoclave sterilizer is provided that includes a coolant tank and a condenser coil extending into the cooling tank. Coolant such as drinkable water flows from a source of coolant into the tank to cool the condenser coil when the temperature of the coolant in the cooling tank exceeds a predetermined value or cooling of the condenser coil is otherwise needed. A drain is in fluid communication with the coolant tank. At least one of an air gap or a check valve is located in a line fluidly between the source of coolant and the waste water drain. The air gap is open to atmospheric air and allows coolant to flow from the source toward the drain but prevents back flow from the drain toward the source by allowing only air to flow from the air gap toward the source. The check valve allows coolant flow in a direction away from the source and prevents flow in an opposed direction toward the source.

Numerous other features of exemplary embodiments will be appreciated upon reading and understanding following description and drawing figures.

DETAILED DESCRIPTION

Figure 1:
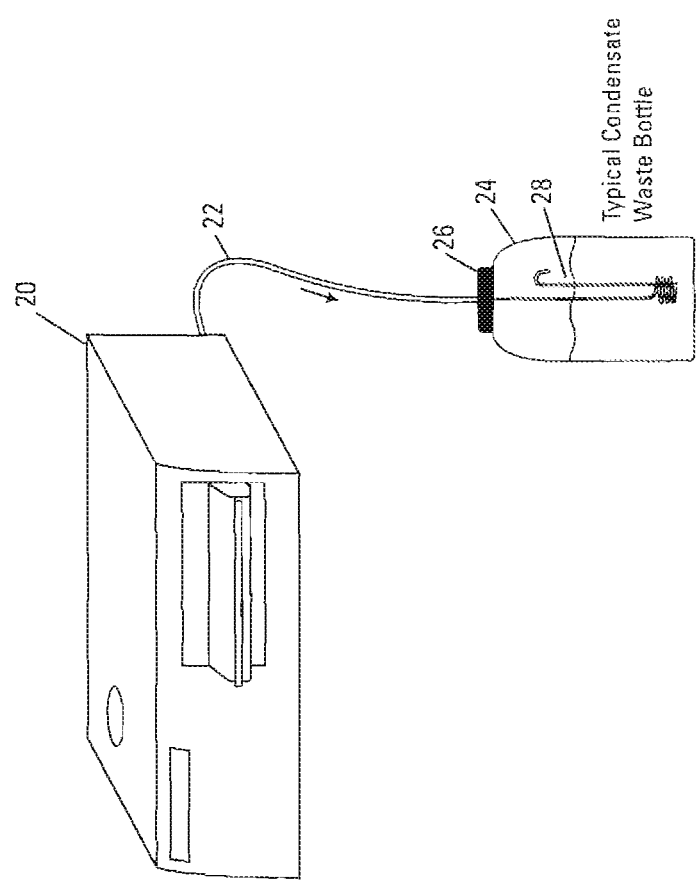
FIG. 1 is a schematic view of a steam condensing system for a cassette style autoclave.

Various technologies pertaining to steam condensing systems will now be described with reference to the drawings, where like reference numerals represent like elements throughout. For purposes of this description, steam condensing will include cooling hot water in combination with steam vapor or hot water phase liquid alone. In addition, several functional block diagrams of example systems are illustrated and described herein for purposes of explanation; however, it is to be understood that functionality that is described as being carried out by certain system components and devices may be performed by multiple components and devices. Similarly, for instance, a component/device may be configured to perform functionality that is described as being carried out by multiple components/devices.

There are generally two types of autoclave sterilizers (cassette and chamber). FIG. 1 shows an exemplary cassette style autoclave 20. Cassette style autoclaves are designed for rapid processing of small volumes of medical, dental or other biological procedure used instruments, which shall be referred to herein as medical or dental instruments. These designs typically utilize a narrow, elongated, clamshell slide-in cassette constructed of stainless steel that holds the instruments to be sterilized. Cassette style autoclaves have a sterilization or heating chamber and a separate small reservoir for distilled-quality water. When a cycle is started, water is delivered to the sterilization cassette and heated to create steam. Once steam is created, the system is pressurized for a specific period of time to kill organisms. When a cycle is complete, steam and very hot water is discharged from the cassette via a drain port while filtered air at ambient temperature is used to begin to cool the cassette and instruments. The steam and condensate flows via a line 22 to a waste bottle 24. The bottle 24 has a cap 26 with an inlet fitting and an internal copper condensing coil 28. A small amount of cool water is to be manually added to the bottle by the user periodically to cover the lower section of the condensing coil 28 to help begin condensation of the steam and cooling of the condensate or water. As the steam is converted to water, the water rises in the condensing coil 28 and drops out of the end directly into the self-contained bottle 24 adding to the water in the bottle 24.

After a few cycles, an attendant or other person has to remove the cap 26 and condensing coil 28 from the bottle 24 to empty the hot water into a sink or other suitable waste water drain. If the attendant forgets, the excess water will escape via a small pressure relief port located in the cap 26. This overflow may cause rotting, warping, delamination and mold in the cabinetry in which the bottle is enclosed. Additionally, if the number of cycles occurs too quickly in succession, the steam may not have time to condense and thus, the steam and water vapor escapes via the relief port hole in cap 26 also creating moisture damage to the enclosure. Further, the effluent waste or condensate from the system may be too hot to discharge directly to plumbing drains. Moreover, it may be a violation of the plumbing codes to discharge steam and/or water too hot for the plumbing system to a waste drain. Also, this type of design may also endanger the attendant who may handle extremely hot equipment.

Figure 2:
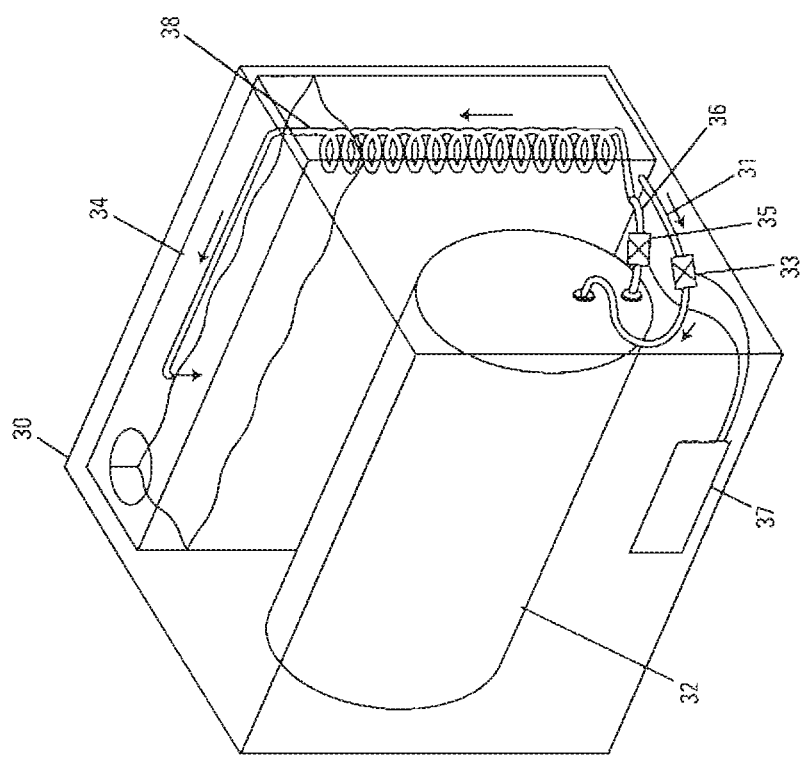
FIG. 2 is a schematic view of a steam condensing system for a chamber style autoclave.

FIG. 2 shows an exemplary chamber style autoclave sterilizer 30. Chamber style autoclaves 30 are designed for processing large numbers of instruments and may have much longer cycle times. These designs typically resemble a large countertop microwave and have a round or square access door on the front of the autoclave 30. They usually have an internal, cylindrical sterilization chamber 32 constructed of stainless steel with multiple shelves that hold trays or wrapped instruments to be sterilized. Chamber style autoclaves 30 may also have a heating chamber and a separate larger reservoir such as a water tank 34 for storing distilled-quality water. When a cycle is started, water is delivered via a line 31 to the sterilization chamber 32 from the water tank by the opening of a solenoid valve 33. The water is heated in the sterilization chamber 32 to create steam. Once steam is created, the sterilization chamber 32 is pressurized for a specific period of time to kill organisms on items in the chamber.

When a cycle is complete, a solenoid valve 35 in a line 36 between the water tank 34 and sterilizing chamber 32 is opened and the steam and very hot water is discharged from the sterilization chamber 32 and sent to the water tank 34 while at the same time filtered ambient temperature enters the chamber 32 to begin cooling the chamber and instruments. The exemplary water tank 34 contains a copper condensing coil 38 that is immersed in the stored water supply and serves to help condense the steam. The opening and closing of the solenoids is operated by circuitry that is referred to herein as a controller 37. The chamber style autoclave 30 may re-use water for many cycles and does not use a waste bottle. Periodically the attendant must physically drain the entire water tank 34 by use of a drain fitting and clean the water tank 34 and sterilization chamber. Fresh distilled-quality water is added back to the reservoir and the process may continue. This type of system often does not present the same problems as the cassette style autoclaves create with use of a waste bottle, but may require a great deal of labor to clean the water tank.

Figure 3:
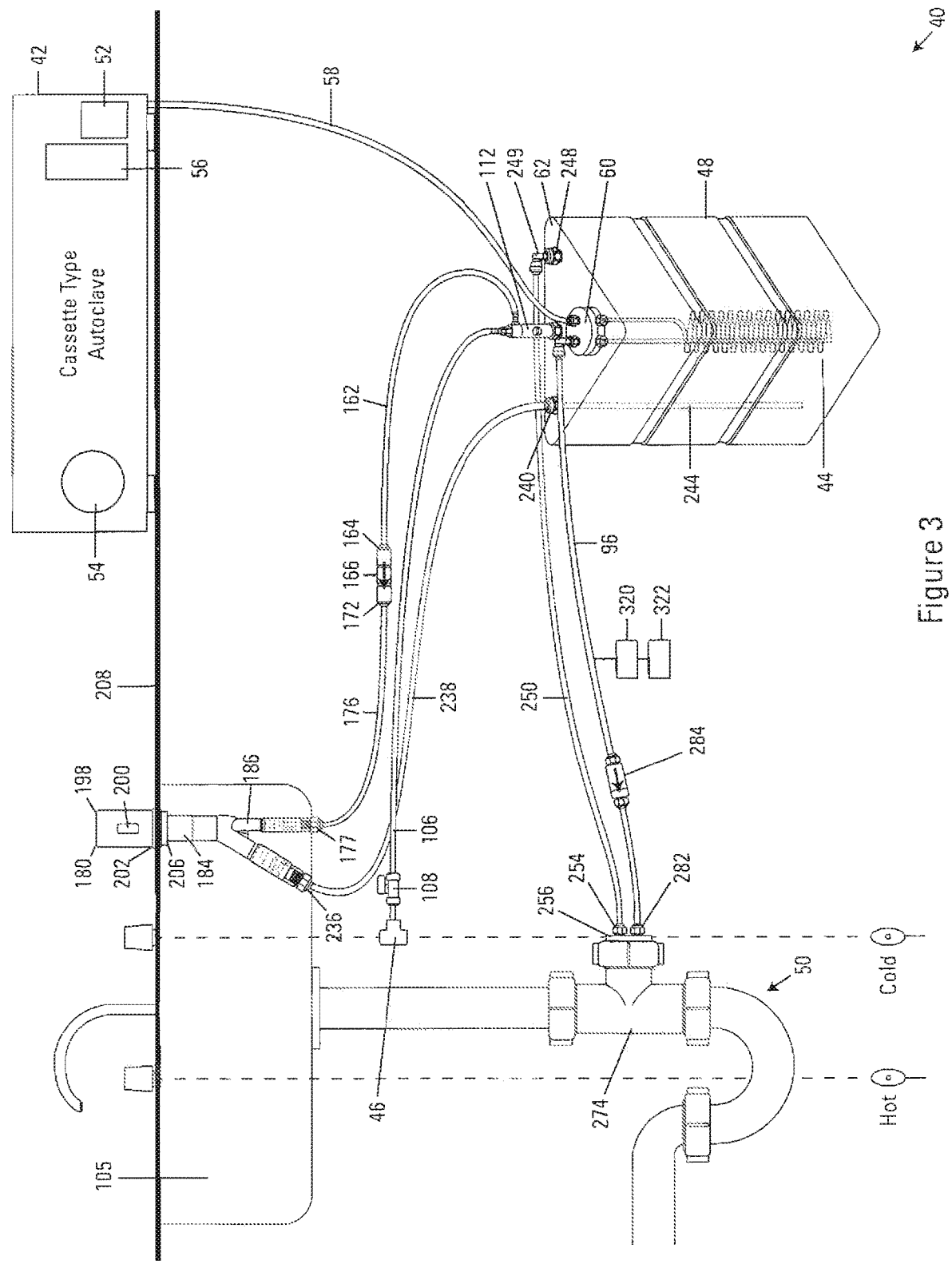
FIG. 3 is a schematic view of a steam condensing system for a cassette style autoclave according to an exemplary embodiment.

Referring to the drawings and initially to FIG. 3, an exemplary embodiment of a steam condensing system 40 is provided that may overcome the above mentioned problems of the steam condensing systems for the autoclaves shown in FIGS. 1 and 2. This steam condensing system 40 is used with a cassette type autoclave sterilizer 42. The condensing system comprises a condenser coil which is alternatively referred to as a condensing coil 44, a source of coolant 46, a coolant or cooling tank 48, and a waste water drain 50. The cassette type autoclave 42 contains the instruments or other objects that are sterilized by steam. The autoclave 42 includes a heating element 52, sterilization chamber 54 and a separate reservoir 56 for distilled-quality water. This water is heated by the heating element 52 to create the steam that is provided in the sterilization chamber 54 used to sterilize the instruments. The sterilization chamber 54 is provided with the steam and is pressurized for a predetermined time to kill organisms.

Figure 4:
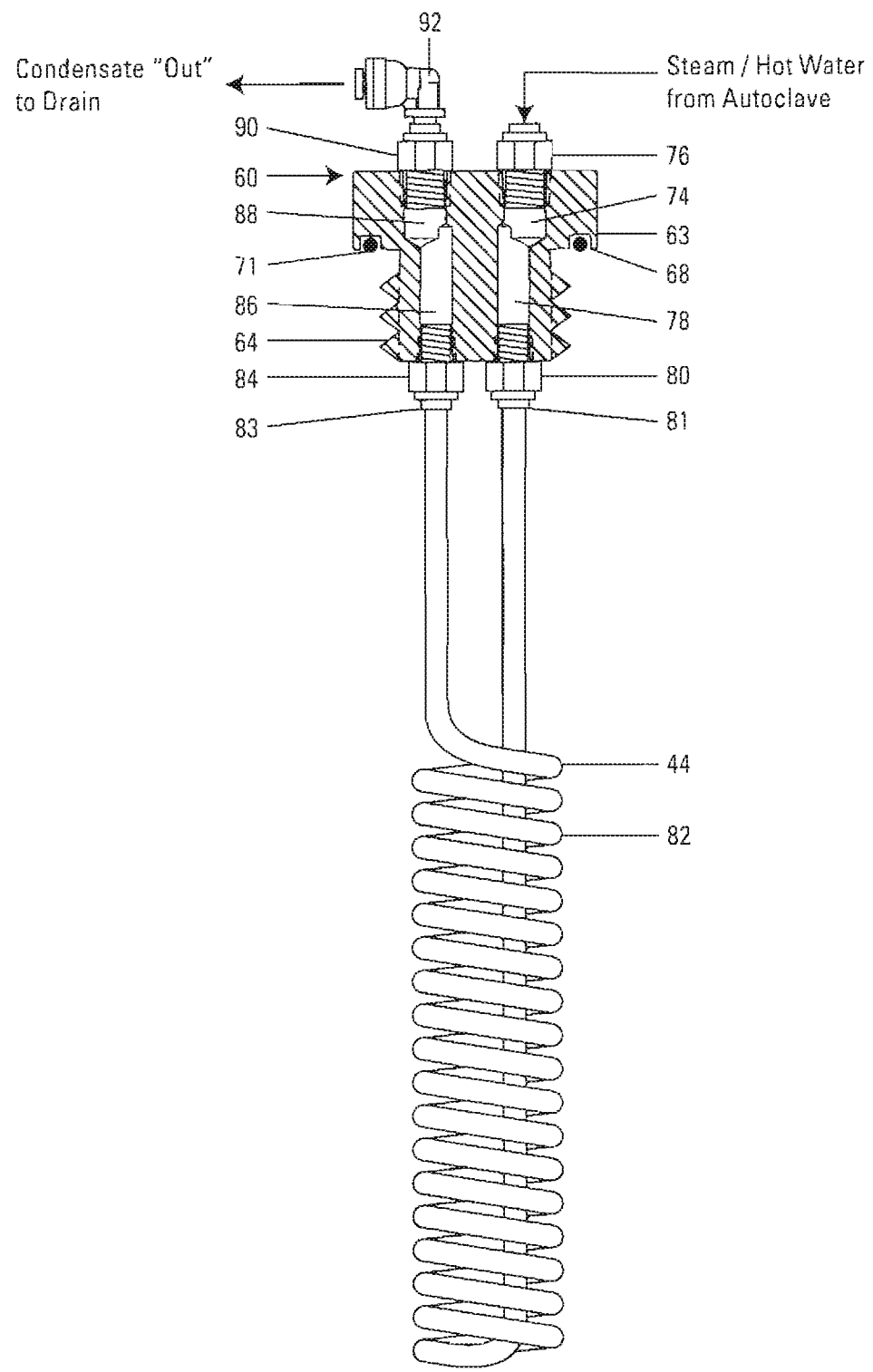
FIG. 4 is a partial front sectional view of a portion of the steam condensing system of FIG. 3 showing the manifold assembled to the condensing coil and related elements.
Figure 5:
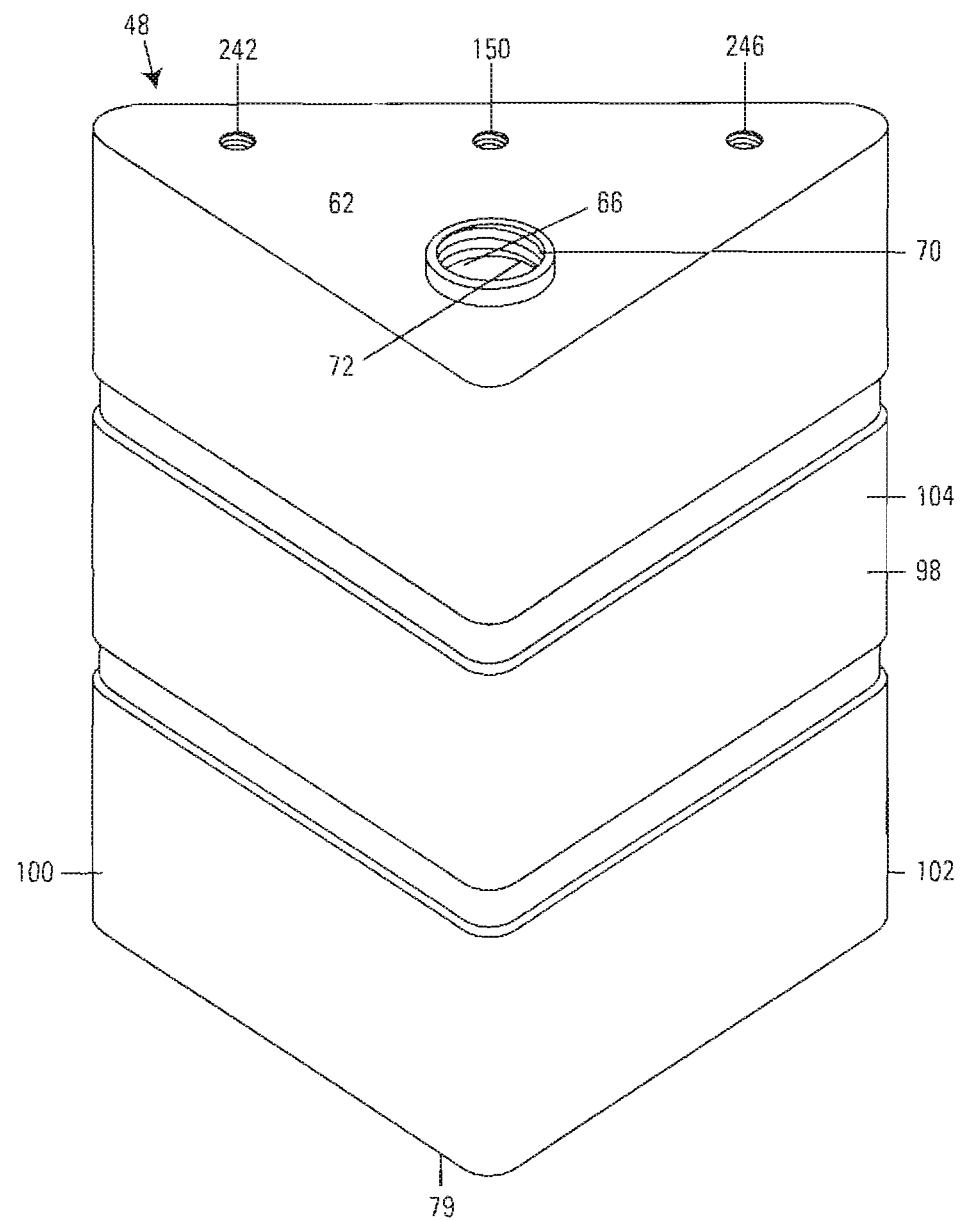
FIG. 5 is a front and top perspective view of the exemplary cooling tank of the steam condensing system of FIG. 3.

A high temperature resistant steam line 58 is fluidly connected between the autoclave 42 and a manifold 60. The manifold 60 is fluidly connected to the condensing coil 44 and releasibly mounted on a top wall 62 of the cooling tank 48. As seen in FIG. 4, the manifold 60 includes a head 63 and connecting body 64. When the manifold 60 is mounted to the cooling tank 48, the connecting body 64 extends through a threaded opening 66 (FIG. 5) into the tank 48 and the head 63 abuts the top wall 62. The opening 66 is sized to enable the coil 44 to be extendable into an interior area of the tank therethrough. The connecting body 64 may have threads that engage threads 72 in the threaded opening 66 to secure the manifold 60 to the top wall 62 of the tank 48. The lower end of the head includes a groove 68 that houses a resilient O-ring gasket that abuts or pushes against a flange 70 (FIG. 5). The flange is attached to the top wall 62 and extends around the opening 66, to seal the manifold 60 to the top wall 62 of the tank 48. The threads 72 may be blow molded, rotocasted, machined, molded or otherwise formed in the tank 48 at the opening 66 to engage the threads of the connecting body 64 to secure the manifold 60 to the top wall of the tank. Alternatively, the manifold 60 may be mounted to the tank 48 by other ways.

For example, the manifold 60 may be bolted to the tank using a bolt down method. The exemplary manifold 60 may be made of polyethylene, polypropylene or other suitable material.

The exemplary manifold 60 includes a first coil inlet port 74 provided on top of the head 63 and is in fluid communication with the steam line 58 (FIG. 3) which is connected to a hot water and steam outlet from the autoclave. The coil inlet port is alternatively referred to herein as a coil inlet. A high temperature resistant Kynar® fitting 76 is fluidly connected to the steam line 58 and is threadibly mounted in the first coil inlet port 74 to provide thermal protection from the steam or hot fluid. The high temperature resistant material may be Kynar®, brass or other suitable material that resists high temperatures. The first coil inlet port 74 fluidly communicates with a first outlet port 78 provided on the bottom of the connecting body 64. The first outlet port 78 is fluidly connected to the condensing coil 44 by a first brass compression fitting adapter 80. The first fitting adapter 80 is secure to the inlet 81 of the condensing coil 44 and threadibly mounted in the first outlet port 78.

The condensing coil 44 is generally comprised of copper or other suitable thermal transfer material and extends downwardly near bottom wall 79 of the cooling tank 48 as seen in FIG. 3. The number of turns 82 on the coil 44 helps the steam to condense as it flows through the coil 44. The number of coils may vary depending on the system. The outlet 83 of the condensing coil 44 is fluidly connected to a second brass compression fitting adapter 84. The second fitting adapter 84 is threadibly mounted in a second input port 86 provided on the bottom of the connecting body 64. The second input port 86 fluidly communicates with a second coil outlet port 88 provided on the top of the head 63 of the manifold 60. The coil outlet port is alternatively referred to herein as a coil outlet. A standard temperature fitting 90 is threadibly mounted in the second outlet port 88 and fluidly connected to an elbow fitting 92. The elbow fitting is fluidly connected to a condensate line 96 (FIG. 3), which in this exemplary embodiment is connected to the waste water drain 50.

Referring to FIG. 5, the exemplary cooling tank 48 is generally comprised of plastic such as polyethyene and is shaped in cross section the form of a right triangle. This shape allows for efficient or space saving placement of the tank in a corner of the cabinet or along a flat surface of a side wall of the cabinet. For mounting the tank to the side wall of the cabinet, the mounting structure may include, for example, threaded inserts in the sides of the tank to receive machine screws, which are hung on a hanger tab mounted on the side wall of the cabinet. The triangular shape design also allows for maximum efficiency for packaging and shipping considerations, since little space is wasted. The coolant tank 48 may be in the form of other shapes to fit into suitable structures. For example, the cooling tank may be rectangular in shape and mounted on the side wall. In some exemplary arrangements the coolant tank may be configured to accept therein two condenser coils. In this manner, a single coolant tank may be utilized to cool steam discharged from two autoclave sterilizers.

The exemplary cooling tank 48 includes the top and bottom walls 62, 79 and right, left, and rear side walls 98, 100, 102 (as viewed in FIGS. 1 and 5). The right and left side walls 98,100 are generally at a right angle with respect to each other. The side walls may include removable plates 104 for additional protection.

The exemplary cooling tank 48 contains coolant such as water that substantially surrounds the condensing coil 44 in a coolant bath to cool the condensing coil 44 and the steam and hot water flowing through the condensing coil 44. The coolant source 46 may be a cold drinkable water line that provides cold water to a sink 105 as shown in FIG. 1. A separate coolant water line 106 is fluidly connected to the cold water line 46. A manually operated in-line shut off valve 108 is provided in the coolant line 106 to selectively allow the flow of water through the coolant line 106 from the cold water line 46. The coolant line 106 is fluidly connected to a barbed inlet 120 (FIG. 6) of a water valve 114 (FIGS. 6 and 7) which in the exemplary embodiment is part of a thermal valve assembly 112.

Figure 6:
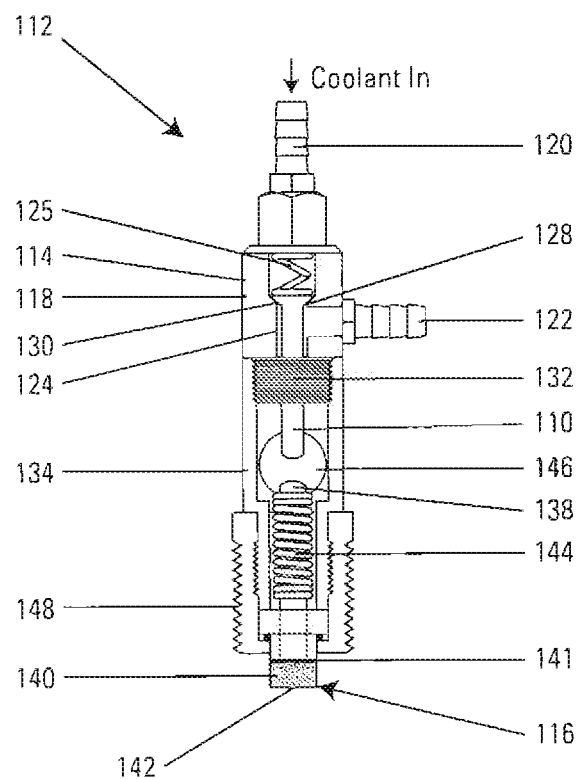
FIG. 6 is a front side view of the exemplary thermal valve assembly of the steam condensing system of FIG. 3 in the closed position with internal portions exposed for purposes of illustration.
Figure 7:
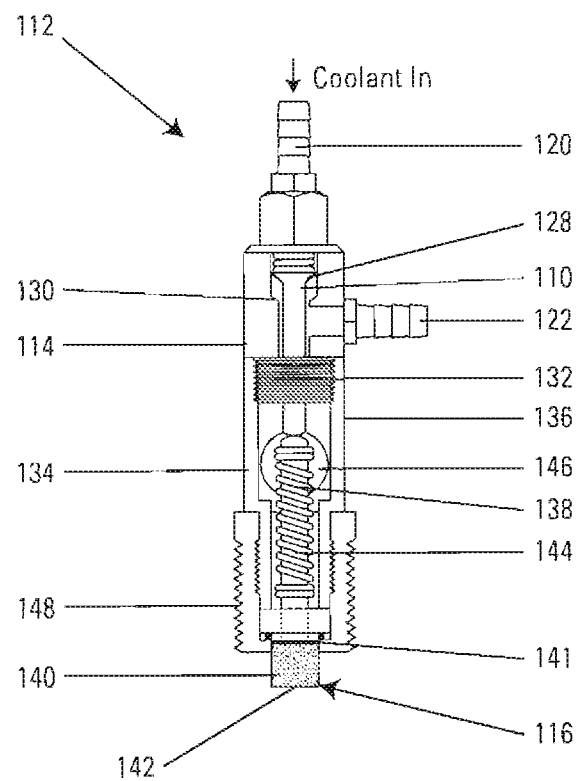
FIG. 7 is a view similar to FIG. 6 but with the thermal valve assembly in the open position.

Referring to FIGS. 6 and 7, the exemplary thermal valve assembly 112 includes the water valve 114 and a thermal actuator 116. The water valve 114 includes a valve body 118, the barbed inlet 120 and a barbed outlet 122. A valve poppet 110 is slidingly received in a bore 124 of the valve body 118. The bore 124 axially extends from the inlet 120 to past the outlet 122. A return spring 125 is provided between the head 128 of the valve 114 and an end portion of the valve body 118 at the inlet 120. The bore 124 is in fluid communication with the inlet 120 and outlet 122. The head 128 of the valve poppet 110 has a larger diameter than that of the bore 124. The valve poppet 110 axially moves between positions within the bore 124 to position the valve 114 between a closed position (FIG. 6) and an open position (FIG. 7). In the closed position of the water valve as seen in FIG. 6, the head 128 of the valve poppet 110 engages the funnel shaped seat 130 of the bore 124 to block the inlet of the bore 124 and prevent water from the coolant line 106 from flowing through the bore 124 and to the outlet 122 of the valve 114. In the open position as seen in FIG. 7, the head 128 of the valve poppet 110 moves upstream off of the seat 130 to allow water to flow from the coolant line 106 into the inlet 120 and the bore 124 and through the outlet 122 of the valve 114. The valve poppet 110 extends through a threaded cylindrical end 132 of the valve body 118. In other exemplary embodiments the water valve may be selectively in condition to provide variable flow rates between the no flow and full flow conditions as appropriate for the flow rate needed through the coolant tank interior area as needed for appropriate cooling of the condenser coil therein.

The exemplary water valve 114 is secured to the thermal actuator 116. In particular, the threaded end 132 of the valve 114 extends into a stem 134 of the thermal actuator 116 and threadibly engages threads in the inner side 136 (FIG. 7) of an end of the stem 134. Alternatively, the stem 134 and the valve body 118 may be attached by other suitable ways or may be formed in one piece. The thermal actuator 116 includes at least one movable part in the form of piston 138 located in the stem 134 and engages wax 140 in a wax cup 142 at the lower end of the piston 138. The wax 140 may be a paraffin wax of an oil base or any other type of wax that expands when heated and contracts when cooled. Other suitable types of material that expand when heated may be used instead of the wax. The piston 138 extends through a return coil spring 144 and is secured to the spring 144. The lower end of the spring 144 is secured to a base or wax cup 142 of the thermal actuator 116. A diaphragm 141 is secured to the wax cup 142 and provided inside the wax cup 142 between the wax 140 and the lower end of the piston 138. The diaphragm 141 may be made of rubber or other suitable flexible material. The wax 140 expands as it is heated and pushes the diaphragm upwardly which in turn flexes and pushes the piston 138 upwardly to flow actuate the water valve. When the temperature in the expanded wax decreases, the wax 140 contracts and the diaphragm retracts back down to allow the return spring 144 to urge the piston 138 downwardly.

In the exemplary embodiments the wax cup and diaphragm or other part or parts that move and change position responsive to temperature, serve as a temperature sensor. The temperature sensor is used in the various embodiments described herein to sense temperature that is indicative of cooling of the condenser coil by the water coolant in the interior area of the coolant tank. In exemplary embodiments the exemplary temperature sensor is in operative connection with the water valve and controls the water flow through the interior area of the coolant tank responsive to the sensed temperature. While in the exemplary embodiment the temperature sensor includes at least one movable part that moves to change its position and the flow condition of the water valve responsive to the sensed temperature, in other embodiments other types of sensors and structures suitable for detecting temperature and changing the flow condition of a water valve in response thereto may be used. This may include, for example, electrical or electronic temperature sensors and electrical solenoids, motors or other types of valve controllers and actuators.

The exemplary embodiment of the valve assembly 112 includes a visual indicator that provides a visual indication of the flow condition of the water valve. The exemplary stem 134 includes a lateral sight opening 146 at the upper end of the piston 138 as shown for viewing the position (actuating or non-actuating) of the piston 138. In an exemplary arrangement the thermal valve assembly 112 is configured such that the valve 114 is placed in the open position when the water in the interior area of the tank is heated to the predetermined temperature that is higher than desirable to help condense the steam. In particular, the water at the sensed predetermined temperature, causes the wax 140 to expand a sufficient amount to overcome the biasing force of the spring 144 and move the piston 138 upwardly as shown until it engages the poppet 110 and moves the head 128 of the poppet off of the seat 130 to allow water to flow from the coolant line 106 into the inlet 120 and the bore 124 and through the outlet 122 of the valve 114. When the water is sensed as below the predetermined temperature value, the valve 114 is in the closed position in which the head 128 engages the seat 130 to block the water from flowing into the bore 124 and through the outlet 122.

The exemplary thermal actuator 116 includes a threaded base 148. In an exemplary arrangement the base is threadibly secured into a threaded opening 150 (FIG. 5) in the top wall 62 of the cooling tank 48 such that the portion of the housing containing the wax cup 142 extends into the water in the interior area of the cooling tank 48.

Figure 8:
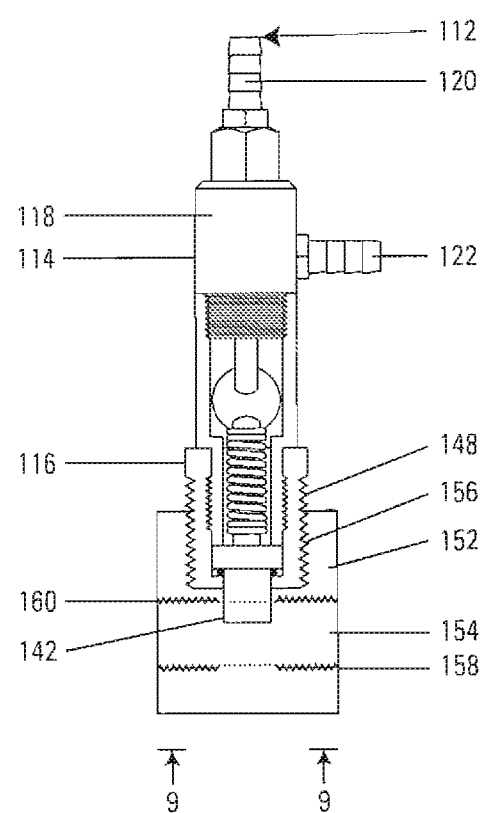
FIG. 8 is a front side view of the thermal valve assembly with the adapter of the steam condensing system of FIGS. 20-22 in the closed position with internal portions exposed for purposes of illustration.
Figure 9:
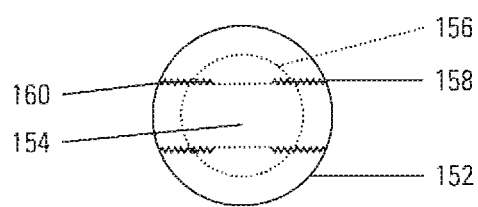
FIG. 9 is an end view from lines 9-9 of FIG. 8.

Referring to FIGS. 8 and 9, a cylindrical adapter 152 may be removably connected to the exemplary thermal valve assembly 112 so that the thermal actuator 116 may be used to monitor the temperature of the water in a line. In particular, the adapter 152 includes a lateral bore 154 extending radially through the adapter 152. The exemplary bore 154 has threaded inlet and outlet ports 158, 160 that are configured to threadibly engage respective male fittings connected to the line.

The adapter 152 also includes a threaded axial bore 156 that is perpendicular to the lateral bore 154 and is in fluid communication with the lateral bore 154. The base 148 of the exemplary thermal actuator is threadibly secured to the axial bore such that the wax cup 142 extends into the lateral bore 154 to sense the temperature of the water or other fluid flowing through the line and the lateral bore 154. The adapter 152 may be made of brass or other suitable material. Of course these approaches are exemplary.

Figure 10:
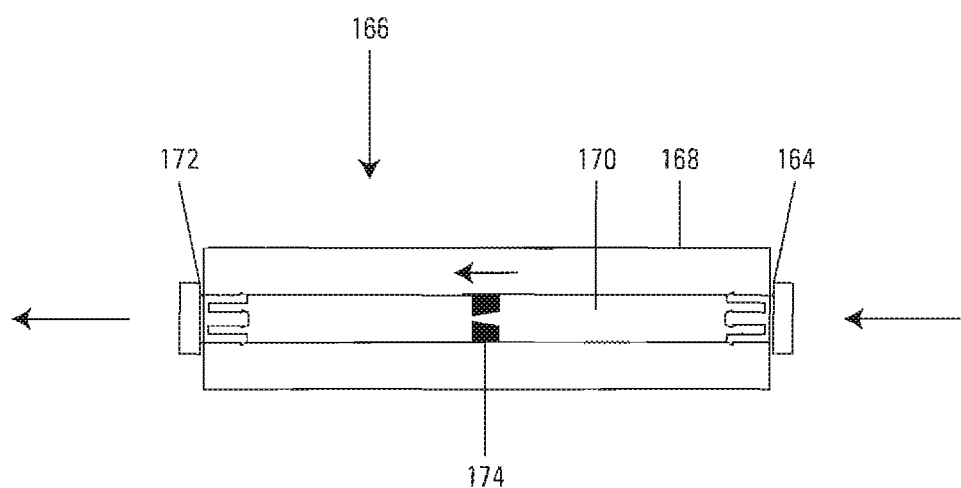
FIG. 10 is a sectional side view of the exemplary flow control device of the steam condensing system of FIG. 3 along the longitudinal axis of the flow control device.

In an exemplary arrangement, a coolant line 162 (FIG. 3) is fluidly connected between the outlet 122 of the valve 114 and an inlet 164 of a flow control device 166, which controls and limits the flow of water to a predetermined value such as 200 or 300 ml/minute. Specifically, as shown in FIG. 10, the flow control device 166 may include a cylindrical housing 168 with an axial bore 170 having the inlet 164 and an outlet 172. A rubber flow control button 174 is provided in the bore 170 and includes an orifice that is configured and sized to control the flow of water at a specific flow rate for a wide range of fluid pressures. The controlled flow of water through the flow control 116 into the cooling tank 48, is set at a level to ensure suitable thermal reduction of the steam and condensate in the condenser coil and delivery of water to the drain at a temperature that does not damage plumbing components while also optimizing and minimizing the use of water.

Figure 11:
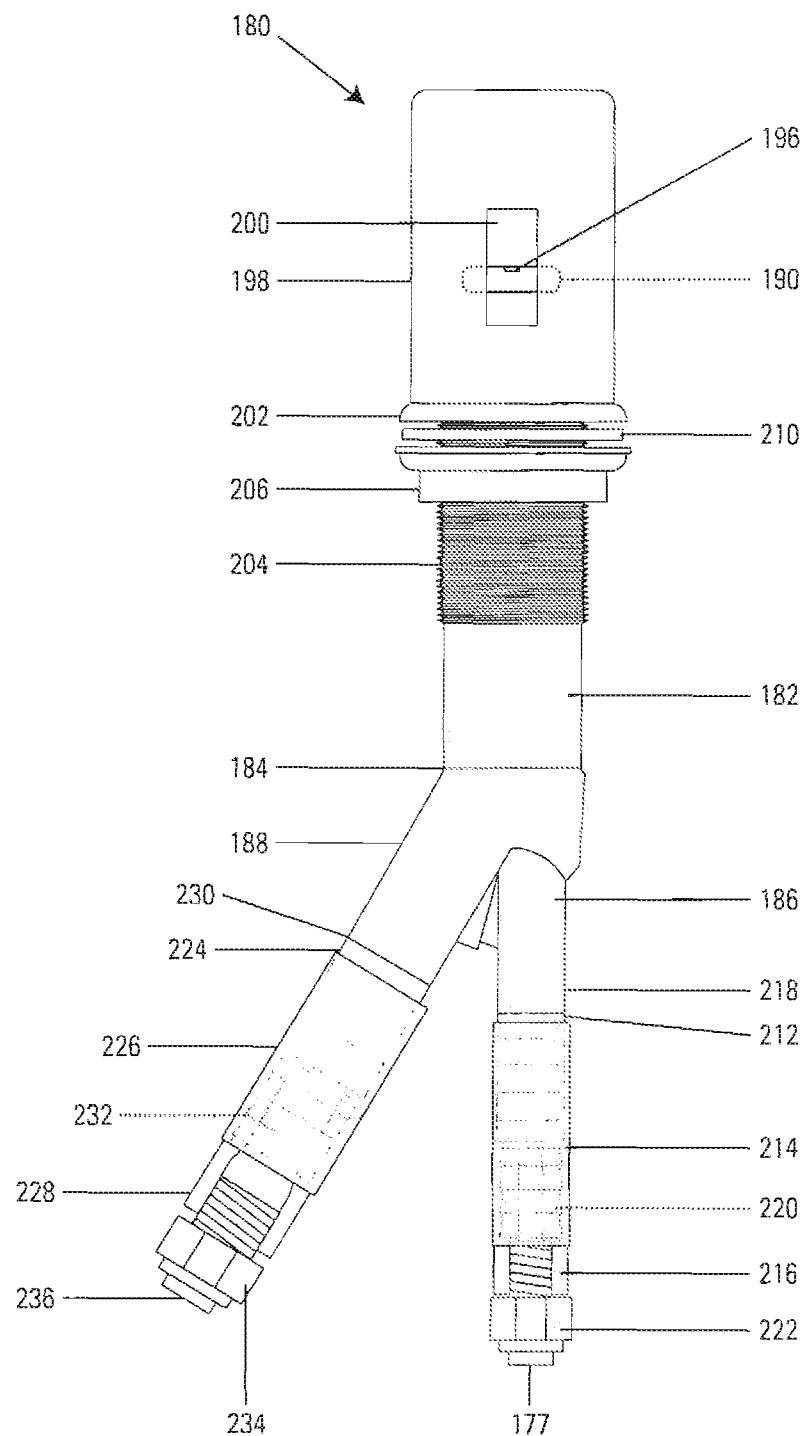
FIG. 11 is a front side view of the exemplary air gap assembly of the steam condensing system of FIG. 3.

Exemplary coolant line 176 is fluidly connected between the outlet 172 of the flow control device and an inlet 177 of an air gap or air gap assembly 180. The air gap assembly is configured to provide an air gap in the water lines that deliver cooling water to the coolant tank in the embodiment shown in FIG. 3. Referring to FIG. 11, the exemplary air gap assembly 180 includes a generally Y-shaped tubular housing 182.

Figure 12:
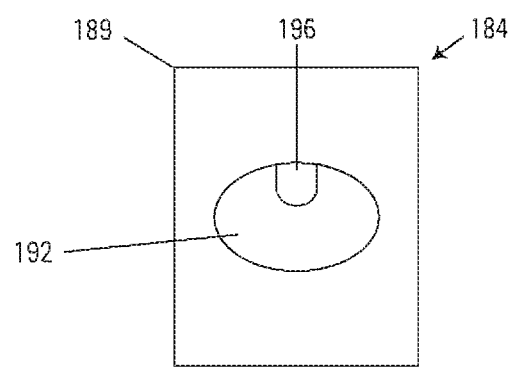
FIG. 12 is a rear side view of the top end of the air gap assembly of the steam condensing system of FIG. 3 with the cover cap removed for illustrative purposes.
Figure 13:
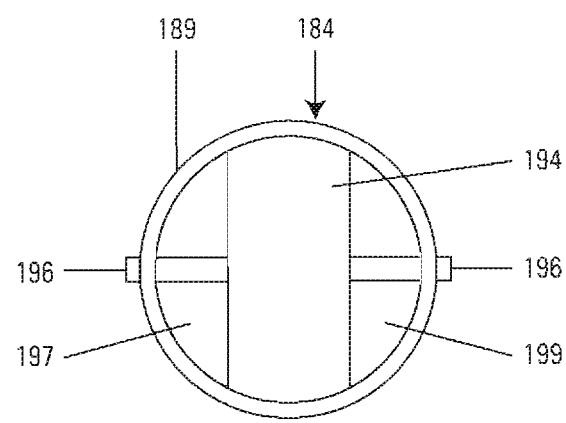
FIG. 13 is a top view of the top end of the air gap assembly of the steam condensing system of FIG. 3 with the cover cap removed for illustrative purposes.

The housing 182 may be made of a thermoplastic material such as Ultra-high-molecular-weight polyethylene or other suitable material. The housing 182 includes a riser tube 184 positioned therein, an inlet branch 186, and an outlet branch 188. The inlet branch 186 is connected to the interior of the riser tube 184. The outlet branch 188 is connected to the interior area of the housing outside the riser tube. The riser tube 184 includes a top end 189 that has an oval shaped lateral water outlet openings 190, 192 (FIGS. 11 and 12) on opposite sides of the top end 189. As seen in FIG. 13, an inner cap 194 is inserted into the top opening of the riser tube 184 and snap fitted to the riser tube 184 by tabs 196 that engage the upper ends of the lateral openings 190, 192. The tabs 196 may be integrally molded on the inner cap 194. The inner cap 194 is spaced radially inward from opposite sides of the riser tube to define arcuate air gaps 197, 199. The inner cap 194 deflects water flowing up the riser to pass out of the lateral openings 190, 192.

Referring to FIG. 11, a decorative cover cap 198 is press fit or friction fit on the top end 189 to cover the top end 189. The cover cap 198 includes a generally rectangular shaped opening 200 that may be angularly aligned over one of the openings 190, 192. The rectangular shaped opening extends vertically below the openings 190, 192. The cover cap 198 is generally cylindrical and may be metallic or chrome like in appearance for aesthetics. The lower end of the cover cap 198 abuts a plastic upper flange nut 202 that threadibly engages a threaded portion 204 on the housing. A plastic lower flange nut 206 threadibly engages the threaded portion 204 downwardly opposite the upper flange nut 202. The flange nuts 202, 206 clamp upon a support surface 208 (FIG. 3) such as the lip of a sink or a countertop to secure the air gap assembly 180 to the support surface 208. The air gap assembly 180 may be configured to fit in the sprayer hole of a standard sink. A rubber washer 210 may be inserted between the upper flange nut 202 and support surface 208.

The inlet branch 186 includes a barbed end 212 that is attached to one end of a tubular adapter 214. The tubular adapter 214 may be made of a flexible clear plastic material such as polyvinyl chloride. A barbed adapter 216 is attached to the other end of tubular adapter 214. The tubular adapter 214 may be attached to the barbed end 212 and the barbed adapter 216 by thermal fusion. For example, the tubular adapter 214 may be heated near its melting point. The melting point of the tubular adapter 214 is lower than that of the barbed end 212 and barbed adapter 216. The barbed end 212 and the barbed adapter 216 are then inserted into their respective ends of the tubular adapter 214. The barbed adapter 216 is inserted such that the barbs 218, 220 in them dig into the inner surface of the tubular adapter 214 so that the melted material of the tubular adapter 214 surrounds the barbs 218, 220. Upon cooling, the melted material hardens to fuse and secure the barbed end 212 and the barbed adapter 216 to the tubular adapter 214. Alternatively, the barbed end 212 and the barbed adapter 216 could be first inserted into the tubular adapter 214 and then have heat applied to the tubular adapter 214 to melt and fuse the plastic material from the tubular adapter 214 to the barbed end 212 and barbed adapter 216.

Alternatively, the barbed end 212 and the barbed adapter 216 may be heated to a temperature near the melting point of the tubular adapter 214. The barbed end 212 and the barbed adapter 216 are then inserted into their respective ends of the tubular adapter 214. The plastic material in the tubular adapter 214 is melted as the barbed end 212 and the barbed adapter 216 are inserted such that the barbs 218, 220 in them dig into the inner surface of the tube so that the melted material surrounds the barbs 218, 220. Upon cooling, the melted material hardens to fuse and secure the barbed end 212 and the barbed adapter 216 to the tubular adapter 214. A tubular fining 222 is threadibly secured into the barbed adapter 216 and serves as the inlet 177 of the air gap assembly 180. The coolant line 176 is fluidly connected to the fitting 222.

The outlet branch 188 also includes a barbed end 224 that is attached to one end of a tubular adapter 226. The tubular adapter 226 may be made of a flexible clear plastic material such as polyvinyl chloride. A barbed adapter 228 is attached to the other end of tubular adapter 226. The tubular adapter 226 may be attached to the barbed end 224 and the barbed adapter 228 by thermal fusion. For example, the tubular adapter 226 may be heated near its melting point. The melting point of the tubular adapter 226 is lower than that of the barbed end 224 and barbed adapter 228. The barbed end 224 and the barbed adapter 228 are then inserted into their respective ends of the tubular adapter 226. The barbed adapter 228 is inserted such that the barbs 230, 232 in them dig into the inner surface of the tubular adapter 226 so that the melted material of the tubular adapter 226 surrounds the barbs 230, 232. Upon cooling, the melted material hardens to fuse and secure the barbed end 224 and the barbed adapter 228 to the tubular adapter 226. Alternatively, the barbed end 224 and the barbed adapter 228 could be first inserted into the tubular adapter 226 and then have heat applied to the tubular adapter 226 to melt and fuse the plastic material from the tubular adapter 226 to the barbed end 224 and barbed adapter 228.

Alternatively, the barbed end 224 and the barbed adapter 228 may be heated to a temperature near the melting point of the tubular adapter 226. The barbed end 224 and barbed adapter 228 are then inserted into their respective ends of the tubular adapter 226.

The plastic material in the tubular adapter 226 is melted as the barbed end 224 and barbed adapter 228 are inserted such that the barbs 230, 232 in them dig into the inner surface of the tube so that the melted material surrounds the barbs 230, 232. Upon cooling, the melted material hardens to fuse and secure the barbed end 224 and the barbed adapter 228 to the tubular adapter 226. Alternatively, the barbed end 224 and the barbed adapter 228 could be first inserted into the tubular adapter 226 and then have heat applied to the tubular adapter 226 to melt and fuse the plastic material from the tubular adapter 226 to the barbed end 224 and barbed adapter 228. Alternatively, the tubular adapter 226 may be heated instead of the barbed end 224 and the barbed adapter 228. A tubular fitting 234 is threadibly secured into the barbed adapter 228 and serves as the outlet 236 of the air gap assembly 180. A coolant line 238 (FIG. 3) is fluidly connected to the fining 234. The exemplary tubular adapters 214, 226 allow for the use of standard male and female plumbing fittings and standard tubing sizes. In other arrangements other types of tube fittings, tube connections and tubing or other fluid conduits may be used.

The exemplary air gap assembly 180 allows incoming water to flow up the inside of the riser tube and out of the lateral openings 190, 192 and air gaps 197, 199 at the top end 189 of the riser 184. The water then flows downward inside the housing on the outside of the riser tube and leaves the housing through the outlet branch 188. In the event water should back flow from the outlet branch into the interior of the housing, the back flow will flow out of opening 200 of the cover cap 198, before reaching the level of openings 190, 192 in the riser tube. This prevents the water from backing up into the water line 46 and causing cross contamination of the drinkable water source and code violations. The openings and air gaps and their location thereof also allow operation of the exemplary cooling system at atmospheric pressure. Of course this air gap configuration is exemplary and in other embodiments other configurations of air gaps may be used.

To install the air gap assembly 180, the cover cap 198 and the upper flange nut 202 are removed and from beneath the sink 105, the riser 184 is inserted into and up through a hole in the support surface 208 until the lower flange nut 206 abuts the underside of the support surface 208. The rubber washer 210 may then be inserted around the riser 184 positioned on top of the support surface 208. The upper flange nut 202 is then threadibly inserted over and down the threaded portion 204 until the upper flange nut 202 rests upon the rubber washer 210. The cover cap 198 is then friction fitted on the riser 184.

Referring to FIG. 3, the coolant line 238 is fluidly connected between the outlet 236 of the air gap assembly 180 and a male connector 240 that is threadibly secured in a threaded coolant inlet opening 242 (FIG. 5) which serves as a tank water inlet in the top wall 62 of the cooling tank 48. A coolant riser 244 is fluidly connected to the male connector 240 and extends downwardly near the bottom wall 79 of the interior area of cooling tank 48. The coolant riser 244 may be made of polypropylene or other suitable material. The coolant inlet opening 242 is located near the left and rear corner of the exemplary cooling tank 48.

As depicted in FIGS. 3 and 5, a threaded coolant overflow opening 246 which serves as a tank water outlet is provided in the top wall 62 of the cooling tank 48 and in the exemplary arrangement as shown is located near the right and rear corner of the cooling tank 48. A male connector 248 is threadibly secured in the overflow opening 246 and is fluidly connected to an elbow 249. The coolant overflow opening 246, the coolant inlet opening 242, and threaded opening 150 for the thermal valve assembly 112 are positioned with respect to each other such that the average water temperature in the cooling tank 48 is monitored by the sensor comprising thermal actuator 116 for more accurate temperature control of the system. In this exemplary arrangement, cool and hot areas in the water of the tank are not separately monitored. In particular, as shown in FIG. 5, the opening 150 is located at the midpoint between the coolant overflow opening 246 and the coolant inlet opening 242 near the rear or hypotenuse side of the cooling tank 48. The opening 150 for the thermal actuator valve assembly is also located rearwardly opposite the opening 66 for the manifold 60, which is located at the front corner of the cooling tank 48 at the junction of the right and left side walls 98, 100. Of course this arrangement is exemplary.

Figure 17:
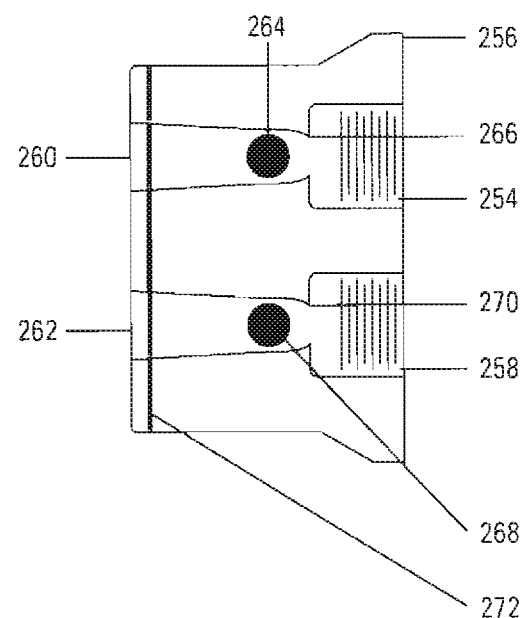
FIG. 17 is a front side sectional view of another drain adapter for the steam condensing system of FIG. 3.

A coolant overflow or drain line 250 (FIG. 3) is fluidly connected to the elbow 249 and a first threaded inlet port 254 of a dual drain adapter 256. The drain adapter 256 may be made of a thermoplastic material such as ultra-high-molecular-weight polyethylene or other suitable material. Referring to FIG. 17, the drain adapter includes first and second threaded inlet ports 254, 258 and first and second outlet ports 260, 262.

The inlet ports 254, 258 have a larger diameter than that of their respective outlet ports 260, 262. The first inlet port 254 is in fluid communication with the first outlet port 260. The first outlet port 260 tapers toward the first inlet port 254. A floating hollow ball 264 is provided in the first outlet port 260 and acts as a check valve to prevent back flow of the water. Specifically, during the normal flow of water the ball 264 is located away from the seat 266 of the first outlet port 260 to allow water to flow to the drain 50 through the space between the first outlet port 260 and the ball 264. If a back flow of water occurs, the water moves the ball 264 toward the seat 266 until it engages the seat 266 to block the water from flowing back to the cooling tank 48.

Figure 16:
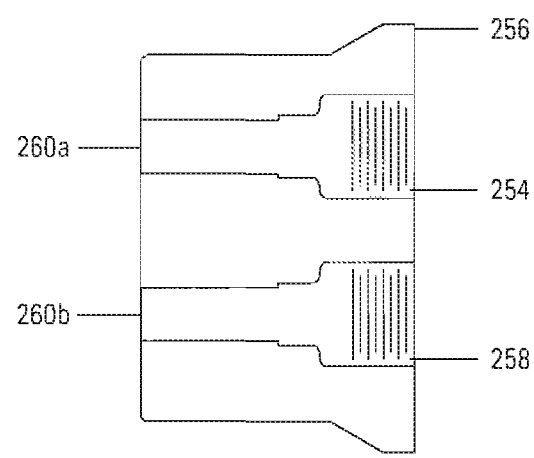
FIG. 16 is a front side sectional view of a drain adapter for the steam condensing system of FIG. 3 that has straight outlet ports.

The second inlet port 258 is in fluid communication with a second outlet port 262. The second outlet port 262 tapers toward the second inlet port 258. A floating hollow ball 268 is provided in the second outlet port 262 and acts as a check valve to prevent the back flow of the water passing to the waste water drain. Specifically, during the normal flow of water, the ball 268 is located away from the seat 270 of the second outlet port 262 to allow water to flow toward the drain 50 through the space between the second outlet port 262 and the ball 268. If a condition that would otherwise cause back flow of waste water out of the drain occurs, the water moves the ball 268 toward the seat 270 until it engages the seat 270 to block the water from flowing toward the cooling tank 48. Both of the balls 264, 268 are retained in their respective outlet ports 260, 262 by a stainless steel drive pin 272. Other types of check valves may be used instead of the ball such as spring loaded poppets. Alternatively, in other embodiments the drain adapter may have straight outlet ports as shown in FIG. 16.

Figure 14:
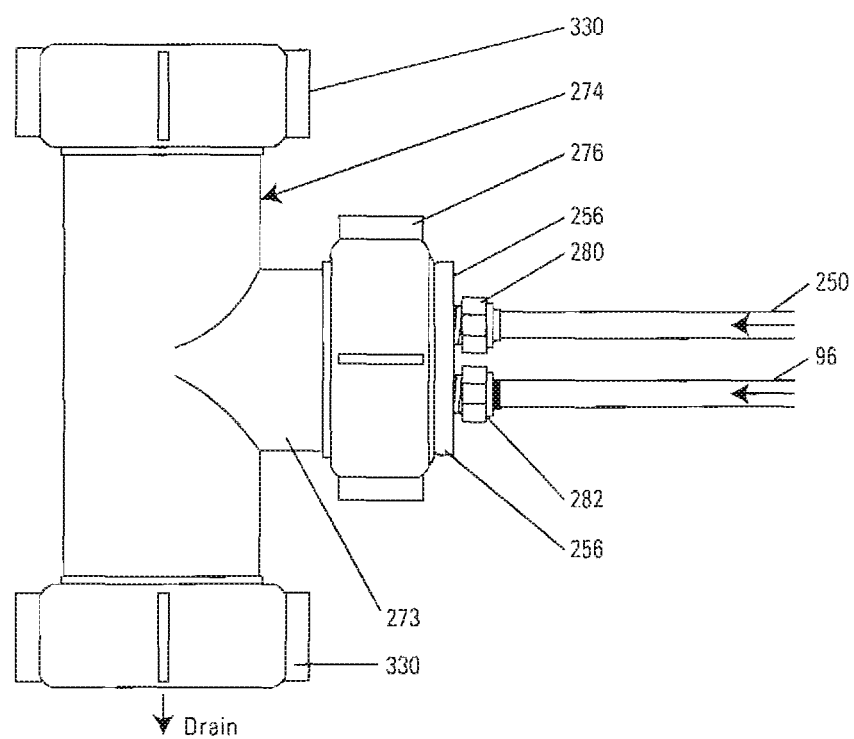
FIG. 14 is a side view of a portion of the steam condensing system of FIG. 3 showing the drain adapter and related elements connected to the slip joint tee, condensate line, and coolant line.
Figure 15:
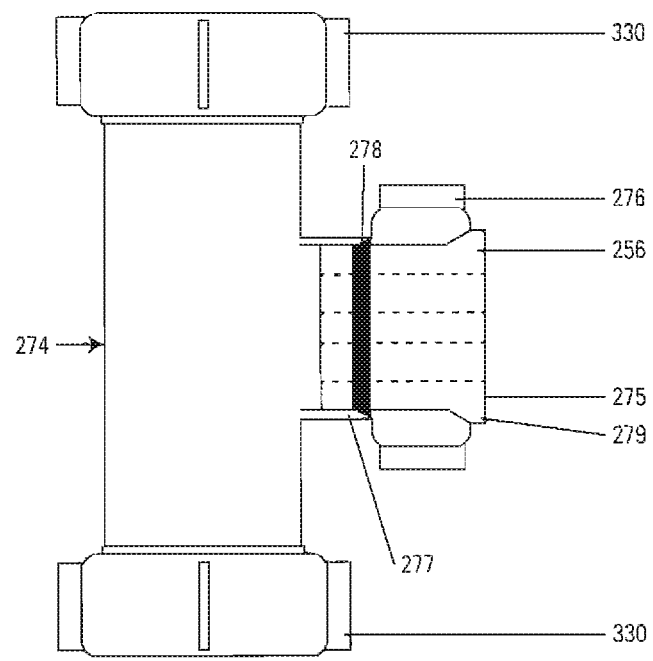
FIG. 15 is a side view of a portion of the steam condensing system of FIG. 3 showing the drain adapter and related elements connected to the slip joint tee and with portions exposed for illustrative purposes.

Referring to FIGS. 14 and 15, the exemplary drain adapter 256 is inserted into an inlet 273 of a slip joint tee 274 that is fluidly connected in the waste water drain line 50 of the sink 105. The drain adapter 256 flares outwardly at its inlet 275 to define a shoulder 279. The shoulder 279 engages a compression nut 276 secured to the inlet 273 of the slip joint tee 274 to prevent further insertion of the drain adapter 256 into the inlet 273. The compression nut 276 is inserted around the inlet 273 and drain adapter 256 and secures the drain adapter 256 to the inlet 273 of the slip joint tee 274. A compression seal washer 278 is provided between the outer surface of the drain adapter 256 and inner surface of the inlet to seal the drain adapter 256 to the inlet 273.

As shown in FIGS. 14 and 17, the first input port threadibly receives a male fitting 280 secured to the overflow line 250 to fluidly connect the overflow line 250 from the coolant tank to the drain adapter 256. The second input port 258 threadibly receives a male fitting 282 to fluidly connect the condensate line 96 from the coil outlet to the drain adapter 256. The exemplary system 40 also includes an in-line thermal valve 284 comprises an assembly that (FIG. 3) located in the condensate line 96 that monitors and blocks condensate flow to the drain 50 if the temperature of the condensate in the condensate line 96 exceeds a predetermined value.

Figure 18A:
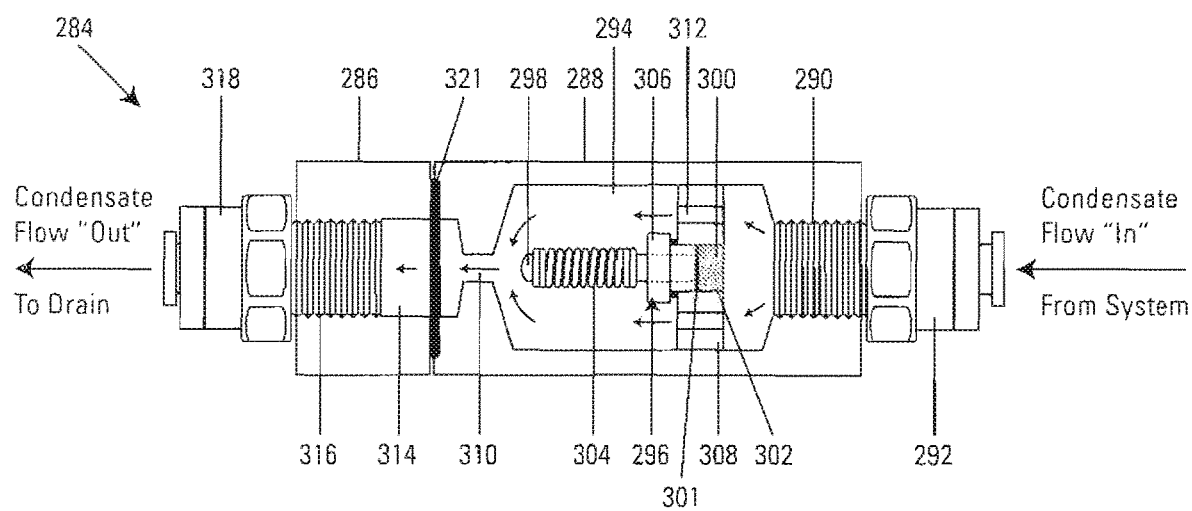
FIG. 18a is a side view of the in-line thermal valve assembly in an open position of the system of FIG. 3 with portions exposed for illustrative purposes.
Figure 18B:
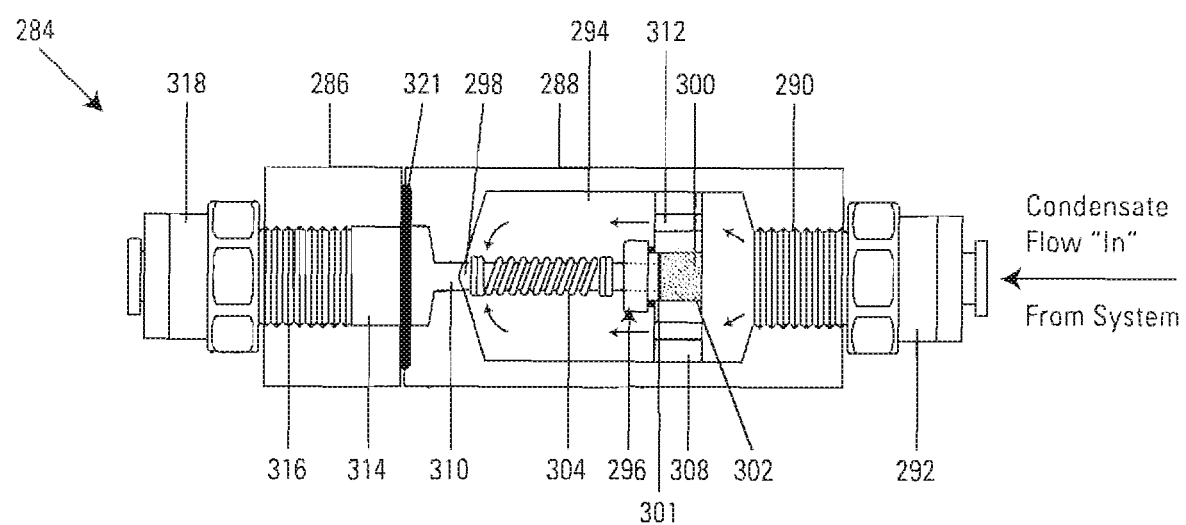
FIG. 18b is a view similar to FIG. 18a but with the in-line thermal valve assembly in a closed position.

Specifically, as seen in FIGS. 18a and 18b, the inline thermal valve assembly 284 includes a cap 286 and a body 288. The body 288 includes a threaded inlet opening 290 that threadibly receives a male fitting 292, which is fluidly connected to the condensate line 96. The inlet opening 290 is in fluid communication with a chamber 294. The chamber 294 houses a thermal actuator 296. The thermal actuator 296 includes a movable piston 298 that engages wax 300 in a wax cup 302 at the upstream end of the piston 298. The wax 300 may be a paraffin wax of an oil base or any other type of wax that expands when heated. Other suitable types of material that expand when heated may be used instead of the wax. The piston 298 extends through a return coil spring 304 and is secured to spring 304. The upstream end of the spring 304 is secured to a base 306 or the wax cup of the thermal actuator 296.

In the exemplary arrangement the wax cup 302 is exposed to the condensate in the chamber 294. A diaphragm 301 is secured to the wax cup 302 and provided inside the wax cup 302 between the wax 300 and upstream end of the piston 298. The diaphragm 301 may be made of rubber or other suitable flexible material. The wax 300 expands as it is heated and pushes the diaphragm 301 which in turn flexes and pushes the piston 298 downstream. When the temperature of the expanded wax decreases, the wax 300 contracts and the diaphragm 301 retracts back down to allow the return spring 304 to urge the piston 298 in the upstream direction. When the temperature in the expanded wax decreases, the wax contracts to allow the return spring 304 to urge the piston 298 in the upstream direction. The exemplary body 288 may be constructed of clear polyvinyl chloride or other clear material for viewing the position of the piston 298. A cylindrical retainer 308 extends around the wax cup and radially extends outwardly to the inner surface of the chamber 294. The retainer 308 holds the thermal actuator 296 in place so that the piston 298 is aligned with an outlet port 310 of the chamber 294. Four bypass holes 312 extend axially through the retainer and are spaced circumferentially equally from each other. The number and size of the bypass holes may vary according to the system.

The cylindrical cap 286 of the exemplary valve includes an inlet opening 314 in fluid communication with a threaded outlet opening 316. The outlet opening 316 threadibly receives a hollow male fitting 318, which is fluidly connected to the condensate line 96. The cap 286 of the in-line thermal valve assembly 284 is threadibly secured to the body 288. An O-ring seal 321 is provided between the cap 286 and the body 288 to seal them from the water.

When the cap 286 and the body 288 are threadibly connected to each other, the outlet port 310 of the chamber is in fluid communication with the inlet opening 314 of the cap 286. During normal operation as shown in FIG. 18*a*, the piston 298 is spaced from the outlet port 310 to place the in-line thermal valve 284 in the open position. In the open position, the condensate from the condensate line 96 flows through the fitting 292 in the inlet opening 258 and into the chamber 294. The condensate then flows through the bypass holes and outlet port of the chamber. The condensate then flows out of the fitting 318 in the outlet opening 316 of the cap 286 and into the condensate line 96 and to the drain 50.

The exemplary thermal actuator 296 is constructed such that when condensate in the chamber 294 is at a predetermined temperature that could cause damage to the elements of the drain, the wax expands and causes the piston 298 to move in the downstream direction and block the outlet port 310 as seen in FIG. 18*b*. This places the in-line thermal valve assembly 284 in the closed position and prevents the condensate from flowing to the drain 50. Of course it should be understood that this approach is exemplary and in other embodiments other types of temperature sensing and valve arrangements that operate to prevent fluid above a set temperature from passing to the waste water drain may be used.

In some embodiments, sensor 320 may also be operatively connected to the in-line thermal valve assembly 284 or condensate line 96 or 396 to detect that the condensate is at or above the predetermined temperature or that the outlet port 310 is blocked by the thermal valve. The sensor 320 may be operatively connected to circuitry including a display 322 and cause the display 322 to display an error message in response to this condition. The sensor 320 circuitry may also be operatively connected to the autoclave and cause the autoclave to stop its current cycle in response to this condition. The sensor 320 may, for example, be a pressure sensor operatively connected to the condensate line 96 that detects back pressure in the condensate line 96 created by the blocking of the outlet port 310 by the piston 298. Alternatively or in addition, the sensor may be operatively connected to a warning light, audible device, or other suitable indicator to indicate that the condensate is at the temperature in which the steam and/or heated water vapor in the condensate line 96 could cause elements of the drainage system to melt or cause damage.

The retraction and resetting of the piston 298 of the exemplary valve may be accomplished by allowing time for the fluid in the chamber to cool or manually by opening the body 288, cooling the wax by use of cold water (which will retract the piston in seconds), placing the wax back into the chamber 294, closing the body 288, and then re-installing the in-line thermal valve assembly 284 in the condensate line 96. The in-line thermal valve assembly size, inlet and outlet connection size, flow rate capacity, and thermal activation set point of the wax motor may all be adjusted as required for use in the specific application.

Referring to FIG. 3, the exemplary system operates as follows. The cooling tank 48 initially contains cold water before sterilization begins. Also, the shut off valve 108 is turned on to allow water to flow to the valve 114 of the thermal valve assembly 112. During sterilization of the instruments in the autoclave, water in the reservoir 56 is heated by the heating element 52 to create the steam that is used to sterilize the instruments. The sterilization chamber 54 containing the instruments is provided with the steam and is pressurized for a predetermined time to kill organisms. The steam is directed through the steam line 58 and through the coil inlet associated with the first inlet and outlet ports 74, 78 of the manifold 60 and into the condensing coil 44. The cold water surrounding the condensing coil 44 cools and causes condensation of the steam traveling through the condensing coil 44. This water in the interior area of the tank is heated by the coil 44 as the steam travels through the coil 44. The steam condenses into condensate which flows through the coil outlet associated with second inlet and outlet ports 86, 88 of the manifold 60 and into the condensate line 96. The condensate then flows through the in-line thermal valve assembly 284 and drain adapter 256 and then to the waste water drain 50.

When the water in the tank interior area is heated to the predetermined temperature that is too high to sufficiently quickly condense the steam and/or that may cause damage to the system from the temperature of the condensate, the thermal actuator 116 operates to place the valve 114 in the open position as previously mentioned. Cool water from the cold water line 46 then flows out of the valve and through the flow control device 166 and the air gap assembly 180. The water then flows down from the air gap assembly 180 by gravity and through the riser tube 244 and into the interior area cooling tank 48. As the cool water flows into the cooling tank 48, the cool water displaces the warmer water which flows out of the tank water outlet including overflow opening 246. The warmer water flows through the overflow line 250, the drain adapter 256 and to the drain 50. This lowers the temperature of the water in the cooling tank 48 to further help condense the steam and lowers the temperature of the condensate to a value that avoids damage to the components of the drain. When the temperature of the water in the cooling tank 48 falls below the predetermined temperature, the wax 140 contracts to place the valve 114 in the closed position to block the cool water from the source and the cold water line from entering the cooling tank 48.

If the water in the cooling tank 48 back flows through the riser 244 and the line 238, the water will flow through the lateral openings 190, 192 and air gaps 197, 199 and out of the opening 200 of the air gap assembly 180. This will also visually alert a user of this condition. The exemplary air gap assembly 180 is designed so that the cooling system operates completely at atmospheric pressure. Since the air gaps and openings in the air gap assembly are at the inlet side of the system (before the cool water flows into the tank), nothing can cross connect and no additional back flow prevention device is needed.

Figure 19:
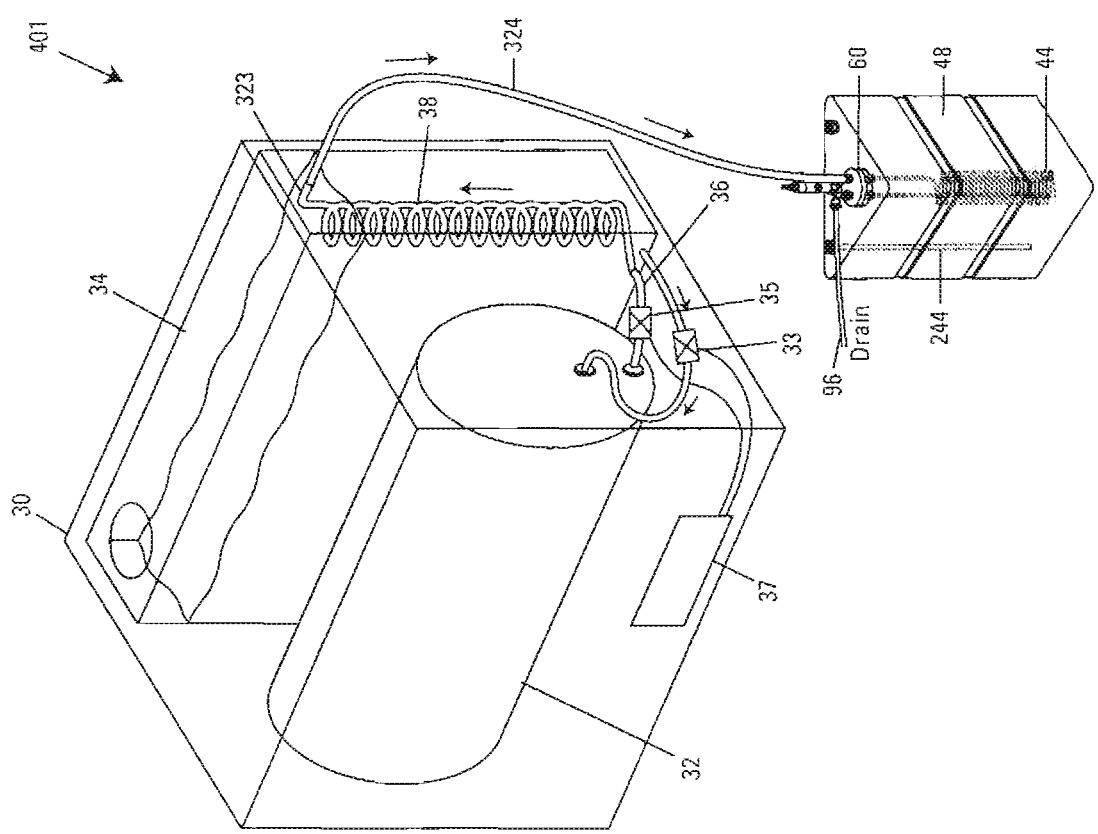
FIG. 19 is a schematic view of a steam condensing system for a chamber style autoclave according to another exemplary embodiment.

FIG. 19 shows another exemplary system 401 that is used with a chamber style autoclave sterilizer. The chamber style autoclave is similar to FIG. 2, except that the outlet 323 of the coil 38 is fluidly connected to the line 324 that is fluidly connected to the inlet port 74 of the manifold 60. This condensing coil 38 serves to further condense the steam and cool the condensate prior to its entry into the cooling tank 48. In this way, less coolant water is used and the entire system stays cooler. Alternatively, the coil 38 may be removed and the line 36 may instead be fluidly connected directly to the inlet port 74 of the manifold 60. In other aspects, the exemplary system is similar in structure and function to that shown and described in FIG. 3.

Figure 20:
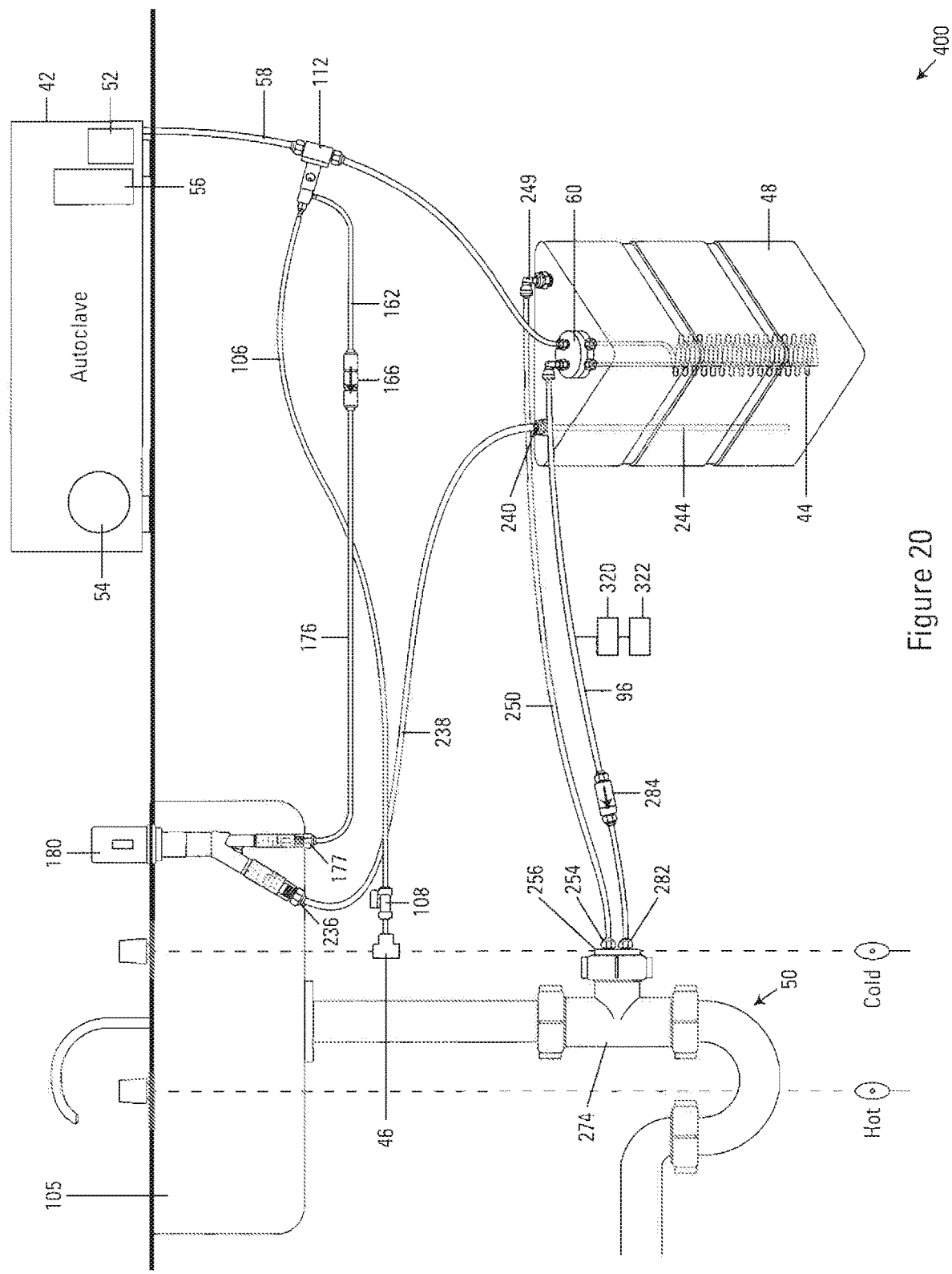
FIG. 20 is a schematic view of a steam condensing system for an autoclave according to another exemplary embodiment.

FIGS. 20-24 show alternative exemplary systems in which the temperature sensor associated with the thermal actuator of the exemplary water valve is operative like the previously described embodiments to sense a temperature at a location in the system indicative of the cooling of the condenser coil by water in the interior area of the coolant tank. FIG. 20 shows an exemplary steam condensing system 400 in which the thermal valve assembly 112 with the cylindrical adapter 152 is fluidly connected in the outlet steam line 58 for monitoring the temperature of the fluid and/or gas being discharged from the autoclave. In operation, when the temperature of the water and/or gas in the steam line 58 is at or above a predetermined temperature, the thermal actuator 116 operates to place the valve 114 in the open position as previously mentioned. Cool water from the cold water line 46 then flows out of the valve 114 and through the flow control device 166 and the air gap assembly 180. The water then flows down from the air gap assembly 180 by gravity and through the outlet branch 188 and into the cooling tank 48. As the cool water flows into the cooling tank 48, the cool water displaces the warmer water which flows out of the overflow opening 246. The warmer water flows through the overflow line 250, the drain adapter 256 and to the drain 50. This lowers the temperature of the water in the cooling tank 48 to further help condense the steam and lowers the temperature of the condensate to a value that avoids damage to the components of the drain 50. When the temperature of the water and/or gas in the steam line 58 falls below the predetermined temperature, the wax 140 contracts to place the valve 114 in the closed position to block the cool water from the cold water line 46 from entering the cooling tank 48. In other aspects, the exemplary steam condensing system 400 is similar in structure and function to that shown and described in FIG. 3.

Figure 21:
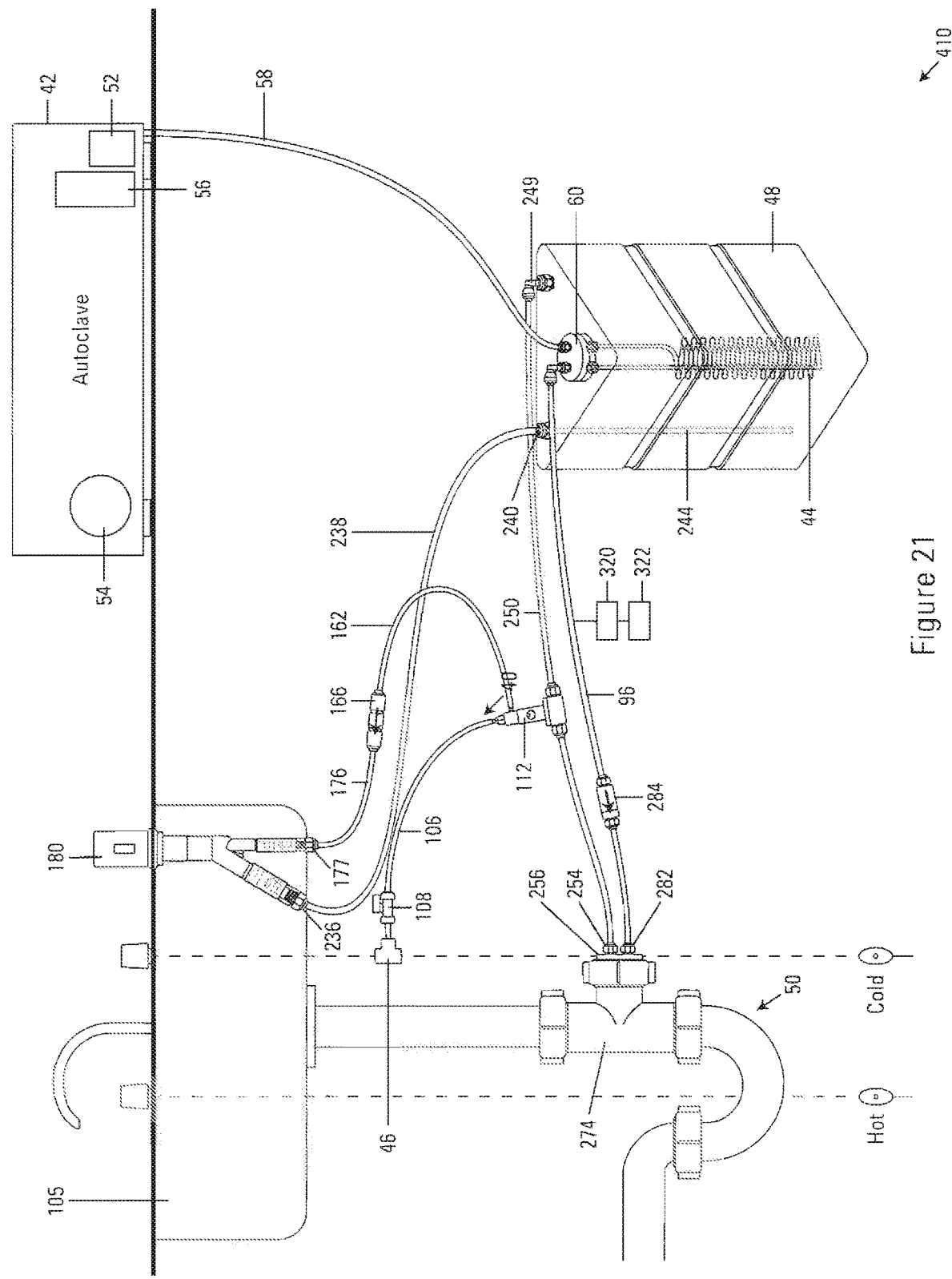
FIG. 21 is a schematic view of a steam condensing system for an autoclave according to another exemplary embodiment.

FIG. 21 shows another exemplary steam condensing system 410 in which the thermal valve assembly 112 with the cylindrical adapter 152 is fluidly connected in the overflow line 250 from the tank water outlet for monitoring the temperature of the water in the line 250 coming from the tank interior area. In operation, when the temperature of the water in the overflow line 250 is at or above a predetermined temperature, the thermal actuator 116 operates to place the valve 114 in the open position as previously mentioned. Cool water from the cold water line 46 source then flows out of the valve 114 and through the flow control device 166 and the air gap assembly 180. The water then flows down from the air gap assembly 180 by gravity and through the outlet branch 188 and into the cooling tank 48. As the cool water flows into the cooling tank 48, the cool water displaces the warmer water which flows out of the overflow opening 246. The warmer water flows through the overflow line 250, the drain adapter 256 and to the drain 50. This lowers the temperature of the water in the cooling tank 48 to further help condense the steam and lowers the temperature of the condensate to a value that prevents damage to the components of the drain. When the temperature of the water in the overflow line 250 falls below the predetermined temperature, the wax 140 contracts to place the valve 114 in the closed position to block the cool water from the cold water line 46 from entering the cooling tank 48. In other aspects, the exemplary steam condensing system 410 is similar in structure and function to that shown and described in FIG. 3.

Figure 22:
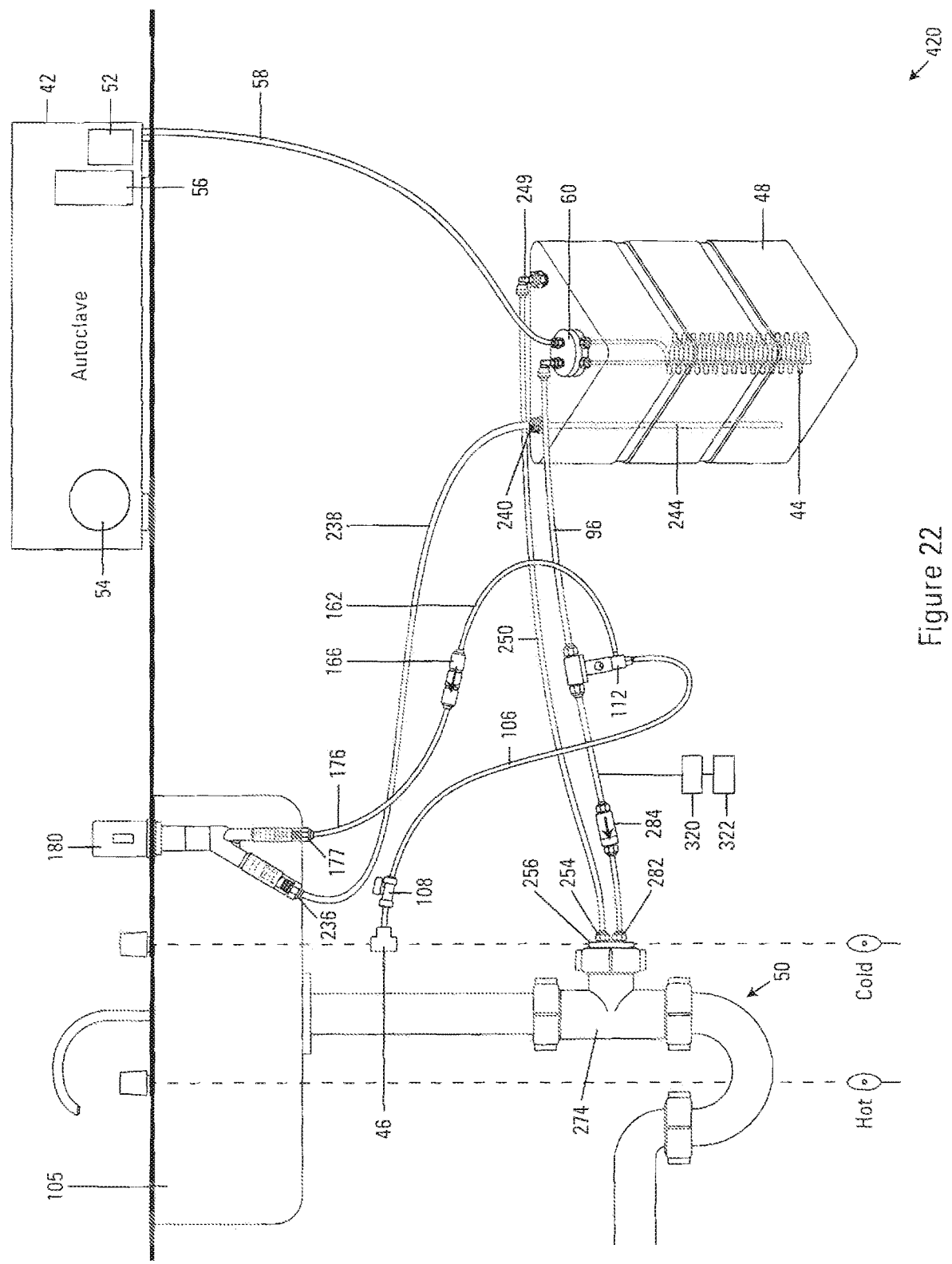
FIG. 22 is a schematic view of a steam condensing system for an autoclave according to another exemplary embodiment.

FIG. 22 shows another exemplary steam condensing system 420 in which the thermal valve assembly 112 with the cylindrical adapter 152 is fluidly connected in the condensate line 96 for monitoring the temperature of the condensate in the line 96. In operation, when the temperature of the condensate in the condensate line 96 is at or above a predetermined temperature, the thermal actuator 116 operates to place the valve 114 in the open position as previously mentioned. Cool water from the cold water line 46 then flows out of the valve 114 and through the flow control device 166 and the air gap assembly 180. The water then flows down from the air gap assembly 180 by gravity and through the outlet branch 188 and into the cooling tank 48. As the cool water flows into the cooling tank 48, the cool water displaces the warmer water which flows out of the overflow opening 246. The warmer water flows through the overflow line 250, the drain adapter 256 and to the drain 50. This lowers the temperature of the water in the cooling tank 48 to further help condense the steam and lowers the temperature of the condensate to a value that avoids damage to the components of the drain. When the temperature of the condensate in the condensate line 96 falls below the predetermined temperature, the wax 140 contracts to place the valve 114 in the closed position to block the cool water from the cold water line 46 from entering the cooling tank 48. In other aspects, the exemplary steam condensing system 420 is similar in structure and function to that shown and described in FIG. 3.

Figure 23:
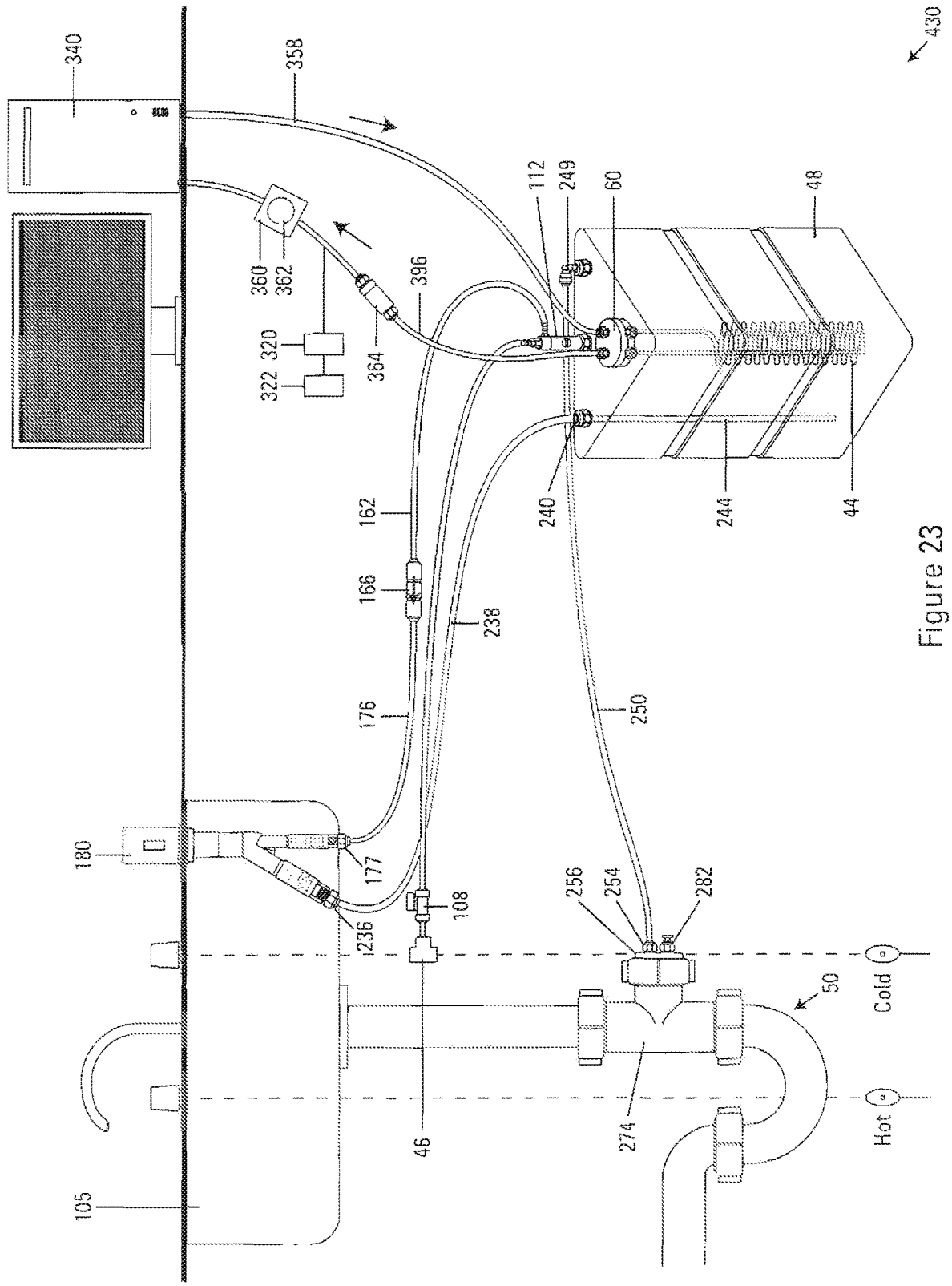
FIG. 23 is a schematic view of a system for liquid cooling a computer according to another exemplary embodiment.

FIG. 23 shows an exemplary system 430 that is used to liquid cool a computer or other heat generating electronic item 340. In this system, liquid used to cool the computer flows through the line 358 and through the first inlet and outlet ports 74, 78 of the manifold 60 and into the condensing coil 44. The cold water surrounding the condensing coil 44 helps cool the liquid traveling through the condensing coil 44. This water is heated by the coil 44 as the liquid travels through the coil 44. The liquid flows through the second inlet and outlet ports 86, 88 of the manifold 60 and into the line 396, which is routed through the computer 340 and is in fluid communication with the line 358. A pump 360 in the line 396 draws the cooled liquid into a reservoir 362 in the line 396 and pumps the liquid through the line 396 to the heat exchanger associated with computer 340 to cool the computer 340. A check valve 364 may be provided in the line 396 upstream of the pump 360 and reservoir 362 to prevent back flow of the liquid. In other aspects, the exemplary system 430 is similar in structure and function to that shown and described in FIG. 3.

Figure 24:
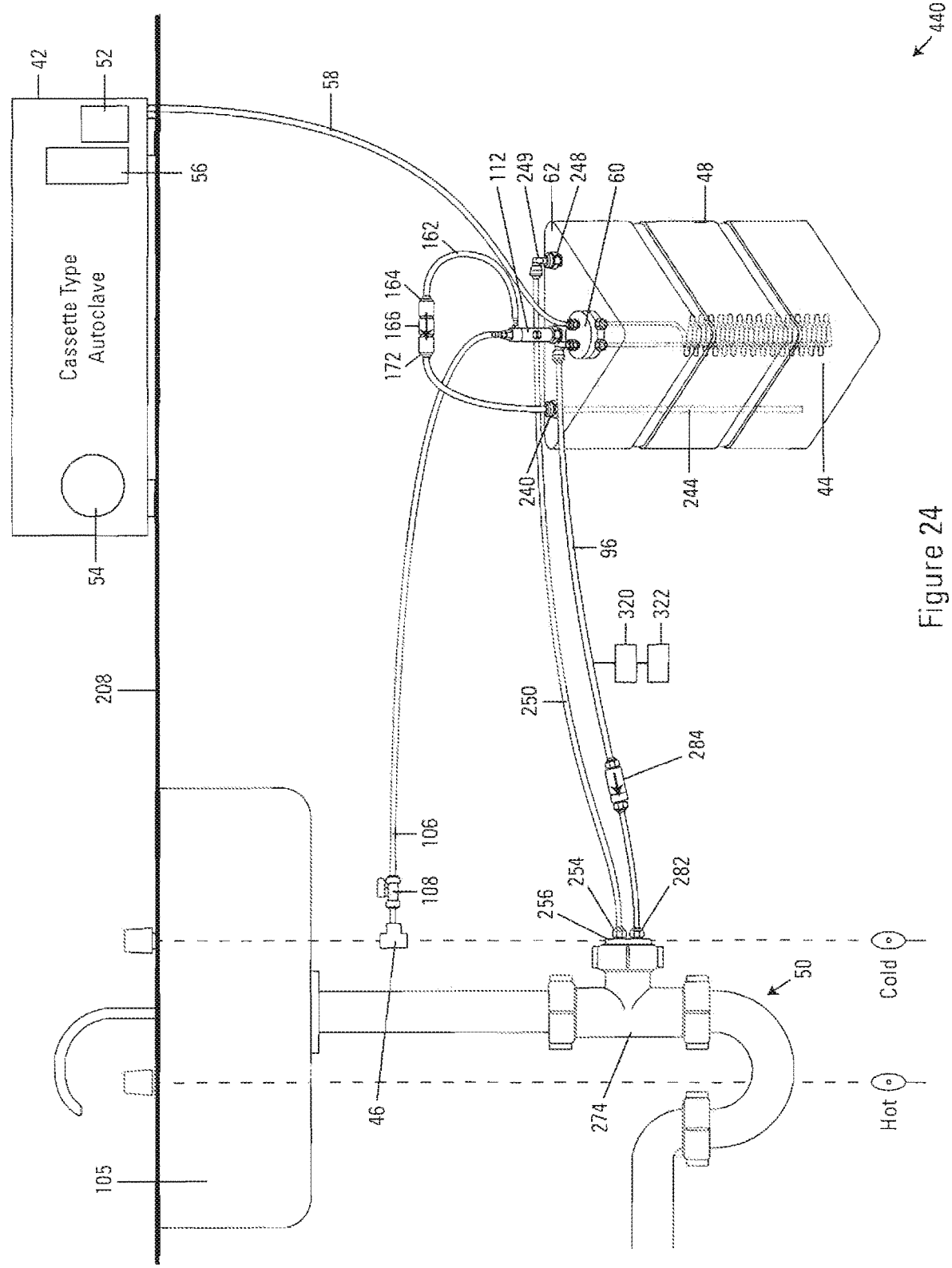
FIG. 24 is a schematic view of a steam condensing system for an autoclave according to another exemplary embodiment.

FIG. 24 shows another exemplary steam condensing system 440 in which the air gap assembly 180 is not used such that the outlet 172 of the flow control device 166 is directly fluidly connected via a line to the male connector 240, which is fluidly connected to the coolant riser 240. In some embodiments a check valve may be positioned in the coolant water lines so as to allow water flow in a direction from the source toward the drain, but prevents flow in an opposed direction toward the source. This may be accomplished by a check valve integrated in the coupling fluidly in operative connection with the coolant line at the drain, such as at the drain adapter previously discussed. Alternatively check valves may be located in other positions in operative connection with the water coolant lines. In some exemplary embodiments a check valve may be connected in a position that is fluidly intermediate of the coolant water source and the coolant tank. This may be done to reduce flow resistance between the coolant tank and the drain. Further in some exemplary arrangements multiple check valves may be used. Check valves may also be used in alternative systems that also include an air gap, which may provide additional protection against back flow conditions. The air gap assembly 180 may also be removed in each of the exemplary embodiments of FIGS. 19-23 such that the outlet 172 of the flow control device 166 is directly fluidly connected via a line to the male connector 240, which is fluidly connected to the coolant riser 244 for each embodiment. In some such arrangements one or more check valves may be in operative connection with at least one water line to prevent back flow as previously discussed. In other exemplary arrangements the flow control device may not be used. The flow control function may be accomplished by the configuration of the water control valve to control and limit coolant water flow. In other exemplary arrangements the check valve may be integral with the water flow control valve to allow flow therethrough only in the direction away from the coolant water source and prevent flow in the opposite direction. Of course these arrangements are exemplary.

Alternatively, in other exemplary embodiments an air gap may exist in water lines in proximity to the waste water drain. For example the drain may incorporate a multiple drain outlet manifold fitting like that shown in the incorporated disclosure of U.S. Provisional Application 62/256,917. Such a drain arrangement may incorporate an air gap within the housing of the drain manifold fitting. The air gap may operate in a manner of previously described air gaps to enable water to flow in a direction toward the drain while preventing water back flow by allowing only air to flow in the opposite direction from the air gap toward the water source, thus reducing the risk of contamination of the source of drinkable water by contaminated water syphoned from the waste water drain. Of course it should be understood that the air gap configurations described herein are exemplary and in other embodiments, other air gap configurations may be used.

An exemplary steam condensing system 40 is installed as follows. First, the cooling tank 48 is filled with cold tap water. The threaded base 148 of the thermal actuator is then threadably inserted into the threaded opening 150 (FIG. 5) in the top wall 62 of the cooling tank 48 and tightened with a wrench such that the wax cup 142 is inserted into the water of the cooling tank 48. The manifold 60 is attached to the condensing coil 44 and the coil 44 is lowered through the threaded opening 66. The manifold 60 is threaded firmly around the threaded flange 70 of the opening 66 such that the lower edge of the manifold 60 and seal is secured tight against the flange 70. The cooling tank 48 is then moved into the cabinet and positioned against a corner or back wall of the cabinet or other structure.

The air gap assembly 180 is installed on the lip of the sink 105 or countertop 208 depending on the sink configuration or other support surface. The air gap assembly 180 is designed to fit in the sprayer hole of standard sinks. If there is no sprayer hole or there is one but the user wishes to keep the sprayer, a hole may be drilled in the lip of the sink or countertop to accommodate the air gap assembly 180. The air gap assembly 180 is installed by first removing the decorative (friction-fit) chrome cover cap 198 by pulling straight upward.

The upper flange nut 202 and washer 210 is then removed from the housing 182 and while the lower flange nut 206 is left intact. From beneath the sink, the housing is inserted into and up through the hole until the lower flange nut 206 abuts the underside of the sink deck or countertop. The rubber washer 210 is pushed down over the housing 182 while pulling up on the housing and riser 184. The upper flange nut 202 is then threaded over and down the housing until the nut 202 has pushed the washer 210 into contact with the sink deck or countertop. The chrome cover cap 198 is fitted over the riser 184 until it locks into place to ensure that it fits properly. The chrome cover cap 198 is then removed. Then, while holding the housing still, tighten the lower flange nut 206 up against the underside of the sink deck or countertop to secure the assembly. Fit the chrome cover cap 198 over the riser 184 and lock into place again.

The drain adapter 256 may then be installed in a vertical or horizontal orientation in the sink drain piping as needed and at a position that is below the air gap assembly 180 and such that the water will not flow out of the lateral openings during normal the flow of water (no back flow). Preferably, the drain adapter 256 is installed at the lowest possible level in the system 40.

To install the drain adapter 256, mark the center point of the area desired for installation, then cut a section of the existing drain tubing out to allow room for the slip joint tee 274. A slip joint compression nut 330 (FIG. 15) over each end of the tubing followed by one beveled washer 277. The beveled edge of the washer is facing the fitting as, for example, depicted in FIG. 15. The slip joint tee 274 is fitted into the open section and the nuts and washers are tightened securely to the threaded ends of the tee. With the beveled washer 277 and compression nut 276 already in place and not yet tightened, the dual port drain adapter 256 is inserted into the inlet 273 of the slip joint tee 274 and pushed until its shoulder 279 is in contact with the nut 276. While tightening the compression nut 276, the drain adapter 256 is pushed towards the slip joint tee 274 until tight. The drain adapter 256 is then rotated so that the second inlet port 258 for the condensate line 96 is below the first inlet port 254 of the coolant overflow line 250. If the slip joint tee 274 is installed horizontally in the plumbing piping, the dual port adapter 256 should always be rotated to the 12 o'clock position so the first and second inlet ports 254, 258 are at the top and discharge downward into the slip joint tee 274. The lines are then connected to their respective elements (e.g. air gap assembly 180, in-line thermal valve assembly 284, flow control device 166, thermal valve assembly 112, manifold 60, coolant riser 244, cooling tank 48, and drain adapter 256) via their respective fittings.

To put the condensing system 40 in its operation mode, the shut off valve 108 is turned on. To test the condensing system 40, a small-bladed, standard screw driver or similar tool is inserted through the sight opening 146 in the side of the thermal actuator stem 134 and moved directly upward upon the poppet 110 to move the poppet upwardly to place the valve in the open position. This action enables fluid actuation of the water valve independent of the temperature sensor and thermal actuator. Held in that position, water should begin flowing from the outlet 122 of the water valve 114, up through the line 162, 176, through the flow control device 166 and into the inlet 177 of the air gap assembly 180. The chrome decorative cover cap 198 from the air gap assembly 180 is temporarily removed by pulling upward. Water should be seen (via the gaps and openings) flowing very slowly into the air gap assembly 180. After a few moments, the water will have filled the riser tube in the air gap assembly 180 and begin flowing from the outlet 236, downward to the coolant riser 244 in the cooling tank 48. The user then temporarily pulls the coolant overflow line 250 out of the fitting 280 at the drain adapter 256 by pushing and holding in a collet around the perimeter while pulling outwardly on the overflow line 250. When a slow, intermittent flow of water is observed flowing from the coolant overflow line 250, the user pushes the line 250 back into the coolant overflow fitting and reassembles the decorative chromed cover cap 198 to the top of the air gap assembly 180. The user then removes the tool used to manually fluidly actuate the water coolant valve 114.

It should be noted that the systems of the exemplary embodiments may be configured to be used for numerous types of thermal transfer of heat between a fluid in a heat exchange device and a fluid surrounding the heat exchange device. For example, the system may be set up to have a container filled with warm water to heat fluid in a heat exchange device. Also, instead of a condensing coil, other types of heat exchange devices that help to cool, condense, or heat up fluids may be used such as a heat sink. Also, a pressure relief device may be used instead of an air gap assembly. The pressure relief device may be an open pressure relief device. Also, various tubing sizes can be Used for the coolant and other lines (e.g. ¼", ⅜", ½", ¾" outer diameter tubing). Numerous different configurations for useful systems may be produced based on the teachings herein.

It is noted that several examples have been provided for purposes of explanation. These examples are not to be construed as limiting the hereto-appended claims. Additionally, it may be recognized that the examples provided herein may be permutated while still falling under the scope of the claims.

Thus the exemplary systems and methods that have been described herein achieve desirable capabilities, eliminate difficulties encountered in the use of prior devices and systems and attain the useful results described herein.

In the foregoing description, in connection with describing exemplary embodiments, certain terms have been used for purposes of brevity, clarity and understanding. However, no unnecessary limitations are to be implied therefrom because such terms are used for descriptive purposes and are intended to be broadly construed. Moreover the descriptions and illustrations of the new and useful features are not limited to the particular features shown and described.

Further it should be understood that elements, features, relationships, devices and other aspects described in connection with one exemplary embodiment may be utilized in connection with other exemplary embodiments such that numerous different arrangements, functions and capabilities are carried out. Numerous different aspects of described embodiments may be used together or in different combinations to achieve useful results.

Having described the features, discoveries and principles of the exemplary embodiments, the manner in which they are constructed and operated, and the advantages and useful results attained, the new and useful structures, devices, elements, arrangements, parts, combinations, systems, equipment, operations, methods, processes and relationships are set forth in the appended claims.

I claim:

1. An apparatus comprising:
  an autoclave sterilizer discharge condenser coil,
    wherein the condenser coil is configured to receive at least one of hot water and steam discharged from an autoclave sterilizer usable to sterilize medical or dental instruments,
  wherein the condenser coil includes
    a coil inlet configured to be in operative connection with the at least one of hot water and steam discharged by the autoclave sterilizer,
    a coil outlet configured to be in operative connection with a condensate water receiver,
  a coolant tank, wherein the coolant tank includes:
    a tank interior area, wherein the condenser coil extends in the tank interior area,
    a tank water inlet to the tank interior area,
    a tank water outlet from the tank interior area,
  a water control valve,
    wherein the water control valve is configured to cause cool water to be selectively delivered to the tank water inlet,
  at least one water line, wherein the at least one water line is in operative connection with
    a source of water,
    the water control valve,
    the coolant tank inlet,
    the coolant tank outlet,
    a waste water drain,
  a temperature sensor, wherein the temperature sensor is in operative connection with the water control valve,
  wherein the water control valve is operative to control an amount of water flow through the tank interior area responsive to a sensed temperature in the interior area of the coolant tank,
  wherein water from the source is enabled to flow through the at least one water line from the source, through the water control valve, through the tank interior area and to the at least one waste water drain, whereby the at least one of hot water and steam in the condenser coil is cooled and condensate water is delivered from the coil outlet,
  at least one of an air gap and a check valve in operative connection with the at least one water line, wherein the at least one of the air gap and the check valve enables water to flow through the at least one water line in a direction from the source toward the waste water drain but not in an opposed direction toward the source.

2. The apparatus according to claim 1
  wherein the coolant tank includes an opening, wherein the sensor releasably extends in the tank interior area through the opening, whereby the sensor is operative to sense temperature of water in the tank interior area.

3. The apparatus according to claim 1
  wherein the at least one water line includes a drain line intermediate of the tank water outlet and the waste water drain, wherein the sensor is operative to sense temperature in the drain line.

4. The apparatus according to claim 1 and further including:
  a condensate outlet line intermediate of the coil outlet and the condensate water receiver,
  wherein the sensor is operative to sense temperature in the condensate outlet line.

5. The apparatus according to claim 1 and further including:
  a condensate inlet line intermediate of the autoclave sterilizer and the coil inlet, wherein the sensor is operative to sense temperature in the condensate inlet line.

6. The apparatus according to claim 1
  wherein the sensor includes at least one movable part that changes position responsive to a temperature of the part,
  wherein the part is in operative connection with the water control valve,
  wherein the amount of water flow through the water control valve is controlled responsive to the part position.

7. The apparatus according to claim 6
  wherein the at least one movable part expands and contracts responsive to the temperature of the part,
  wherein the water control valve includes a poppet and a valve seat,
  wherein expansion and contraction of the at least one movable part is operative to change the position of the poppet relative to the valve seat which is operative to change the amount of water flow through the water control valve.

8. The apparatus according to claim 7
  wherein the at least one movable part includes a wax material.

9. The apparatus according to claim 6 and further including:
   a visual indicator in operative connection with the water control valve,
   wherein the visual indicator is operative to indicate a current flow condition of the water control valve.

10. The apparatus according to claim 9
   wherein the visual indicator includes a sight opening, wherein a position of the at least one movable part is visible through the sight opening, and wherein the water control valve is flow actuatable independent of the at least one movable part through the sight opening.

11. The apparatus according to claim 9 and further including
   a condensate manifold, wherein the condensate coil is in operative connection with the condensate manifold and the manifold includes the coil inlet and the coil outlet,
   wherein the coolant tank includes a manifold opening, wherein the condenser coil is removably extendable in the tank interior area through the manifold opening,
   wherein the condensate manifold is releasably engageable in the manifold opening.

12. The apparatus according to claim 11
   wherein the manifold opening includes a threaded opening,
   wherein the condensate manifold is releasably threadably engageable in the threaded opening.

13. The apparatus according to claim 12
   wherein the tank includes an annular flange in surrounding relation of the threaded opening,
   and further including an annular resilient seal,
   wherein the seal extends in sealing relation of the flange and the manifold when the manifold is engaged with the coolant tank via the manifold opening.

14. The apparatus according to claim 11
   wherein the condensate water receiver includes the waste water drain,
   and further including a thermal valve, wherein the thermal valve is positioned intermediate of the coil outlet and the waste water drain,
   wherein the thermal valve is operative to prevent fluid above a set temperature from passing from the coil outlet to the waste water drain.

15. The apparatus according to claim 11
   wherein the condensate water receiver includes a liquid reservoir in operative connection with the autoclave sterilizer, wherein liquid from the reservoir is heated by the autoclave.

16. The apparatus according to claim 11 and further including the air gap
   wherein the air gap includes a housing, wherein the housing is open to atmosphere and the air gap extends within the housing, and wherein the air gap allows only air to flow in the opposed direction.

17. The apparatus according to claim 11 and further including the air gap,
   wherein the air gap includes an assembly, wherein the assembly includes a housing and a riser tube extending vertically within the housing and having at least one riser upper opening,
   wherein the housing is open to atmospheric pressure, and water flows into the housing via the riser tube, out the at least one upper opening and leaves the housing from an area between the riser tube and the housing below the at least one riser upper opening.

18. The apparatus according to claim 11 and further including the check valve, wherein the check valve is positioned fluidly intermediate of the source and the tank water inlet.

19. The apparatus according to claim 1 wherein the coolant tank is triangular in cross section.

20. The apparatus according to claim 1
   wherein the coolant tank is triangular in cross section.

21. The apparatus according to claim 1 and further including the check valve, wherein the check valve is positioned in fluid communication with the source and the tank water inlet.

22. The apparatus according to claim 1, wherein the water control valve is flow actuatable responsive to the temperature sensor.

23. The apparatus according to claim 22
   wherein the water control valve is operative to control the amount of water flow through the tank interior area responsive to a sensed temperature.

24. The apparatus according to claim 1, and further including at least one of
   (a) an opening in the coolant tank, wherein the sensor releasably extends in the tank interior area through the opening and is operative to sense temperature of water in the tank interior area,
   (b) a drain line intermediate of the tank water outlet and the waste water drain, wherein the at least one water line includes the drain line, and wherein the sensor is operative to sense temperature in the drain line,
   (c) a condensate outlet line intermediate of the coil outlet and the condensate water receiver, wherein the sensor is operative to sense temperature in the condensate outlet line, and
   (d) a condensate inlet line intermediate of the autoclave sterilizer and the coil inlet, wherein the sensor is operative to sense temperature in the condensate inlet line.

25. The apparatus according to claim 1, wherein the water control valve is independent of the temperature sensor.

26. An apparatus comprising:
   an autoclave sterilizer discharge condenser coil, wherein the condenser coil is configured to receive at least one of hot water and steam discharged from an autoclave sterilizer usable to sterilize medical or dental instruments, wherein the condenser coil includes a coil inlet configured to be in operative connection with the at least one of hot water and steam discharged by the autoclave sterilizer, and a coil outlet configured to be in operative connection with a condensate water receiver,
   a coolant tank, wherein the coolant tank includes: a tank interior area, wherein the condenser coil extends in the tank interior area, a tank water inlet to the tank interior area, and a tank water outlet from the tank interior area,
   a water control valve, wherein the water control valve is configured to cause cool water to be selectively delivered to the tank water inlet,
   at least one water line, wherein the at least one water line is in operative connection with a source of water, the water control valve, the coolant tank inlet, the coolant tank outlet, and a waste water drain,
   a condensate manifold, wherein the condensate coil is in operative connection with the condensate manifold and the manifold includes the coil inlet and the coil outlet, wherein the coolant tank includes a manifold opening, wherein the condenser coil is removably extendable in the tank interior area through the manifold opening, wherein the condensate manifold is releasably engageable in the manifold opening, at least one of an air gap and a check valve in operative connection with the at least one water line, wherein the at least one of the air gap and the check valve enables water to flow therethrough in a direction from the source toward the waste water drain but not in an opposed direction toward the source, and wherein water from the source is enabled to flow through the at least one water line from the source, through the water control valve, through the tank interior area and to the at least one waste water drain, whereby the at least one of hot water and steam in the condenser coil is cooled and condensate water is delivered from the coil outlet.

27. An apparatus comprising:

an autoclave sterilizer discharge condenser coil, wherein the condenser coil is configured to receive at least one of hot water and steam discharged from an autoclave sterilizer usable to sterilize medical or dental instruments, wherein the condenser coil includes a coil inlet configured to be in operative connection with the at least one of hot water and steam discharged by the autoclave sterilizer, and a coil outlet configured to be in operative connection with a condensate water receiver, wherein the condensate water receiver includes a waste water drain, a coolant tank, wherein the coolant tank includes: a tank interior area, wherein the condenser coil extends in the tank interior area, a tank water inlet to the tank interior area, a tank water outlet from the tank interior area, a water control valve, wherein the water control valve is configured to cause cool water to be selectively delivered to the tank water inlet, at least one water line, wherein the at least one water line is in operative connection with a source of water, the water control valve, the coolant tank inlet, the coolant tank outlet, and the waste water drain, at least one of an air gap and a check valve in operative connection with the at least one water line, wherein the at least one of the air gap and the check valve enables water to flow therethrough in a direction from the source toward the waste water drain but not in an opposed direction toward the source a thermal valve, wherein the thermal valve is positioned intermediate of the coil outlet and the waste water drain, wherein the thermal valve is operative to prevent fluid above a set temperature from passing from the coil outlet to the waste water drain, wherein water from the source is enabled to flow through the at least one water line from the source, through the water control valve, through the tank interior area and to the at least one waste water drain, whereby the at least one of hot water and steam in the condenser coil is cooled and condensate water is delivered from the coil outlet.

28. An apparatus comprising:

an autoclave sterilizer discharge condenser coil, wherein the condenser coil is configured to receive at least one of hot water and steam discharged from an autoclave sterilizer usable to sterilize medical or dental instruments, wherein the condenser coil includes a coil inlet configured to be in operative connection with the at least one of hot water and steam discharged by the autoclave sterilizer, and a coil outlet configured to be in operative connection with a condensate water receiver, a coolant tank, wherein the coolant tank includes: a tank interior area, wherein the condenser coil extends in the tank interior area, a tank water inlet to the tank interior area, a tank water outlet from the tank interior area, a water control valve, wherein the water control valve is configured to cause cool water to be selectively delivered to the tank water inlet, at least one water line, wherein the at least one water line is in operative connection with a source of water, the water control valve, the coolant tank inlet, the coolant tank outlet, and the waste water drain, an air gap in operative connection with the at least one water line, wherein the air gap and enables water to flow therethrough in a direction from the source toward the waste water drain but not in an opposed direction toward the source, wherein the air gap is included in an assembly, wherein the assembly includes a housing and a riser tube extending vertically within the housing and having at least one riser upper opening wherein the housing is open to atmospheric pressure and water flows into the housing via the riser tube, out the at least one upper opening and leaves the housing from an area between the riser tube and the housing below the at least one riser upper opening, wherein water from the source is enabled to flow through the at least one water line from the source, through the water control valve, through the tank interior area and to the at least one waste water drain, whereby the at least one of hot water and steam in the condenser coil is cooled and condensate water is delivered from the coil outlet.

* * * * *